United States Patent
Lu et al.

(10) Patent No.: US 9,447,103 B2
(45) Date of Patent: Sep. 20, 2016

(54) INAUHZIN ANALOGUES THAT INDUCE P53, INHIBIT CELL GROWTH, AND HAVE ANTITUMOR ACTIVITY

(71) Applicant: Indiana University Research and Technology Corp., Indianapolis, IN (US)

(72) Inventors: Hau Lu, Metairie, LA (US); Shelya Zeng, Metairie, LA (US); Qi Zhang, Metairie, LA (US); Qizhuang Ye, Carmel, IN (US); Derong Ding, Mishiwaka, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 14/417,471

(22) PCT Filed: Jul. 27, 2013

(86) PCT No.: PCT/US2013/052430
§ 371 (c)(1),
(2) Date: Jan. 26, 2015

(87) PCT Pub. No.: WO2014/018953
PCT Pub. Date: Jan. 30, 2014

(65) Prior Publication Data
US 2015/0197522 A1    Jul. 16, 2015

Related U.S. Application Data

(60) Provisional application No. 61/676,694, filed on Jul. 27, 2012.

(51) Int. Cl.
| | |
|---|---|
| *C07D 487/04* | (2006.01) |
| *A61K 31/53* | (2006.01) |
| *A61K 31/704* | (2006.01) |
| *A61K 33/24* | (2006.01) |
| *A61K 31/5377* | (2006.01) |
| *A61K 31/538* | (2006.01) |
| *A61K 31/5415* | (2006.01) |
| *A61K 45/06* | (2006.01) |
| *C07D 519/00* | (2006.01) |

(52) U.S. Cl.
CPC ............ *C07D 487/04* (2013.01); *A61K 31/53* (2013.01); *A61K 31/538* (2013.01); *A61K 31/5377* (2013.01); *A61K 31/5415* (2013.01); *A61K 31/704* (2013.01); *A61K 33/24* (2013.01); *A61K 45/06* (2013.01); *C07D 519/00* (2013.01)

(58) Field of Classification Search
CPC ...................................................... C07D 487/04
See application file for complete search history.

(56) References Cited

U.S. PATENT DOCUMENTS

| 2005/0271747 A1 | 12/2005 | Higgins et al. |
| 2011/0257184 A1 | 10/2011 | Qu et al. |

FOREIGN PATENT DOCUMENTS

| WO | WO 2012/135149 | * 10/2012 |

OTHER PUBLICATIONS

Zhang, Feb. 13, 2012, EMBO Mol. Med, vol. 4, p. 298-312.*
Golub, 1999, Science, vol. 286, p. 531-537.*
Targeted Cancer Therapies, retrieved Dec. 8, 2015, http://www.cancer.gov/about-cancer/treatment/types/targeted-therapies/targeted-therapies-fact-sheet.*
International Search Report and Written Opinion dated Dec. 3, 2013 from related International Application No. PCT/US2013/052430.
AC1NUV9U—Compound Summary (CID 5494506) Jul. 29, 2005 p. 1 formula.
AC1NREAJ—Compound Summary (CID 5289939), Apr. 14, 2005.

* cited by examiner

*Primary Examiner* — Rebecca Anderson
*Assistant Examiner* — Karen Cheng
(74) *Attorney, Agent, or Firm* — Faegre Baker Daniels LLP

(57) ABSTRACT

Inauhzin (INZ) was identified as a novel p53 activator, which selectively and efficiently suppressing tumor growth without displaying genotoxicity and with little toxicity to normal cells. A panel of INZ analogs were synthesized and evaluated their ability to induce cellular p53 and to inhibit cell growth in cell-based assays. As described, this leads to the discovery of INZ analog 37, a molecule that exhibits much better potency than INZ in both of p53 activation and cell growth inhibition in several human cancer cell lines including H460 and HCT116$^{+/+}$ cells. This INZ analog exhibited a much lower effect on p53-null H1299 cells and importantly no toxicity towards normal human p53-containing WI-38 cells. Those results also reveal key chemical features for INZ activity, and identify the newly synthesized INZ analog 37 as a better small molecule for further development of anti-cancer therapies.

8 Claims, 19 Drawing Sheets

Scheme 1

Scheme 2

Scheme 3

Scheme 4

(h) Propargyl bromide or 4-bromo-1-butyne, K₂CO₃ or Cs₂CO₃, DMF, rt; (i) 2-bromoacetophenone, K₂CO₃, DMF, rt; (j) azide derivative, sodium ascorbate, CuSO₄, t-BuOH/H₂O, 55°C Inauhzin (INZ), 1

INAUHZIN ANALOGUES THAT INDUCE P53, INHIBIT CELL GROWTH, AND HAVE ANTITUMOR ACTIVITY

CROSS-REFERENCE TO RELATED APPLICATIONS

This application is a U.S. National Phase Patent Application based on International Application No. PCT/US2013/052430 filed Jul. 27, 2013, which claims the benefit of U.S. Provisional Patent Application No. 61/676,694 filed Jul. 27, 2012, the entire disclosures of which are hereby expressly incorporated herein by reference.

FIELD OF THE INVENTION

Aspects of the invention include compounds related to the molecule inauhzin and methods of synthesizing and using the same to inhibit the growth of cells including cancer cells.

BACKGROUND AND SUMMARY

The p53 tumor suppressor protein can prevent the formation of tumors through several mechanisms, including the activation of cell-cycle checkpoints to prevent damaged cells from proliferation (cell-cycle arrest and DNA repair), the promotion of senescence (permanent cell-cycle arrest), and/or the triggering of cell death (apoptosis or autophagy). It can also impede cell migration, metabolism, or angiogenesis, which are needed for cancer cell progression and metastasis. Mutations of the tumor suppressor gene TP53 are detected in ~50% of all types of human cancers, while the functions and stability of the p53 protein are often abrogated via posttranslational mechanisms in the rest of human cancers that contain wild type TP53. Therefore, the restoration or reactivation of wild-type p53 function can lead to rapid elimination of tumors. As such, compounds that target the p53 pathway have become promising anticancer drug candidates, and several of them have entered clinical trials. For instance, Nutlin-3 and MI-219 can increase p53 level and activity by interfering with the p53-MDM2 binding. Even though there have been extensive endeavors to find small molecules that target the p53 pathway, none has yet proven to be clinically effective therapeutics due to the inherent undesirable toxicity to normal cells and tissues.

Recent efforts in silico screening and cellular-based assays have shown that Inauhzin (INZ) and some of its analogs (FIG. 7) comprise a class of small molecules that effectively activate p53 and promote p53-dependent apoptosis of human cancer cells, apparently without causing genotoxic stress. In addition, INZ appears to stabilize p53 by increasing p53 acetylation and preventing MDM2-mediated ubiquitylation of p53 in cells. Remarkably, INZ inhibited cell proliferation, induced senescence and tumor-specific apoptosis, and repressed the growth of xenograft tumors derived from p53-harboring lung cancer H460 and colon cancer HCT116$^{+/+}$ cells without causing measurable toxicity to normal tissues.

INZ is an effective anti-cancer agent which can be used either alone or in combination with Nutlin treatment or DNA damage agents such as Cisplatin and Doxorubicin. A single treatment with Nutlin-3 is less efficient in inhibiting the growth or in promoting apoptosis of some cancer cells, such as HCT116$^{+/+}$, H460, or A549, in xenograft tumor models even though these cells contain wild type p53. The combination of INZ with Nutlin-3 synergistically promotes apoptosis in HCT116$^{+/+}$ and H460 cell lines in a p53-dependent fashion. This combination also synergistically activates p53 in xenograft tumors derived from these cancer cells and significantly suppresses their growth.

To further characterize the structural features essential for the activity of this group of small molecules to induce p53 and to suppress cell proliferation, a structure-activity relationship (SAR) analyses of INZ analogs was performed. A number of new INZ analogs were synthesized and evaluated for their ability to induce p53 and inhibit cell growth using cell-based assays. This study not only revealed critical chemical groups for INZ activity, but also lead to the discovery of INZ derivative 37, a compound that displays better potency in p53 induction and cancer cell growth inhibition than does INZ.

Additional information regarding small molecule modulators of SIRT1 activity activating p53 and suppressing tumor growth can be found in International Patent Application Publication Number WO 2012/135149, published Aug. 20, 2009 base on PCT/US/2012/030619 having an International Filing Date of Mar. 26, 2012, which claims the benefit of U.S. provisional patent Applications Nos. 61/467,511 filed on Mar. 25, 2011, 61/579,519 filed on Dec. 22, 2011, and 61/583,040 filed on Apr. 1, 2012, each of which are hereby incorporated by reference in their entirety.

According to one embodiment of the present disclosure, a composition is provided, the composition comprising a compound according to Formula (I) or a pharmaceutically acceptable salt thereof:

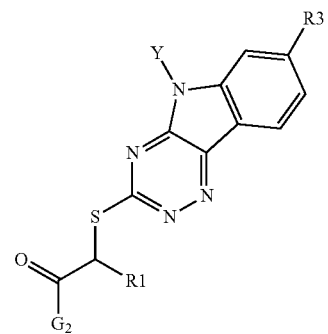

Formula (I)

wherein, $G_2$ is:

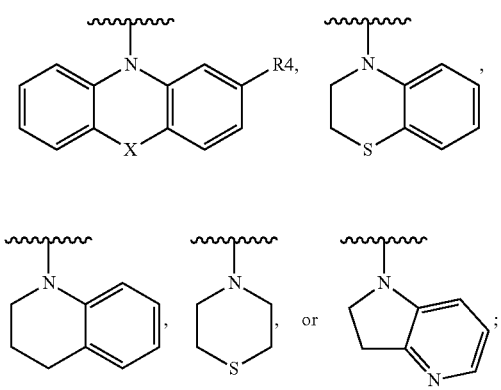

X is: CH₂, O, NH, or S;
R1 is: CH₃, CH₃CH₂, CH₃CH₂CH₂, or CH₃CH₂CH₂CH₂;
Y is: H,

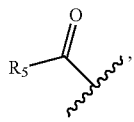

or R2;
R2 is:

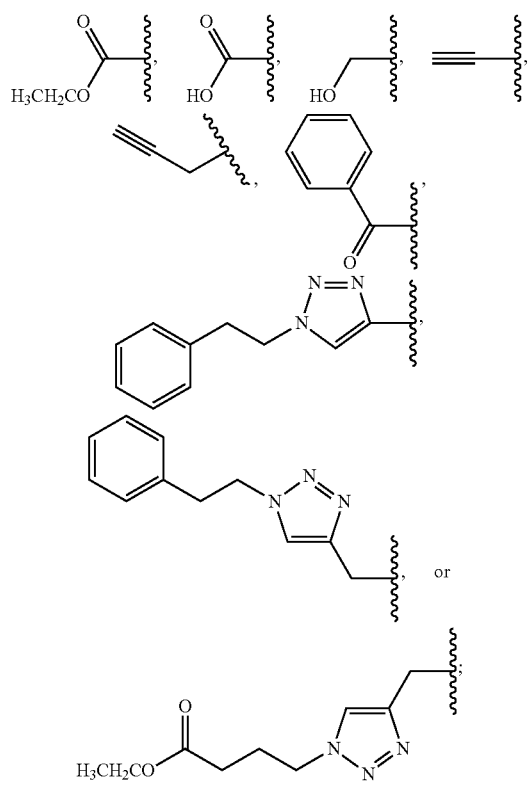

R3 is H, an alkyl group, or a halogen;
R4 is H, a halogen, or OCH₃; and
R5 is:

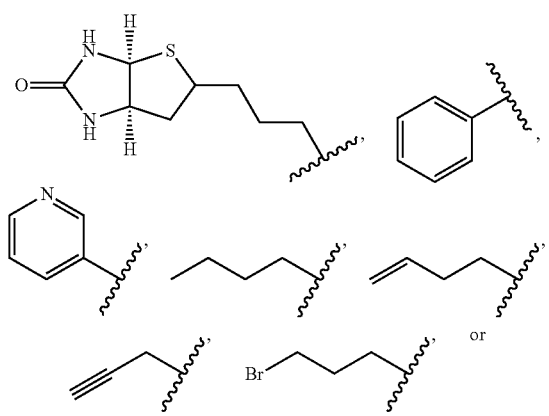

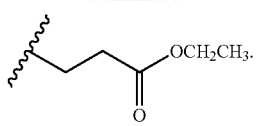

In one particular embodiment, the compound according to Formula I is:

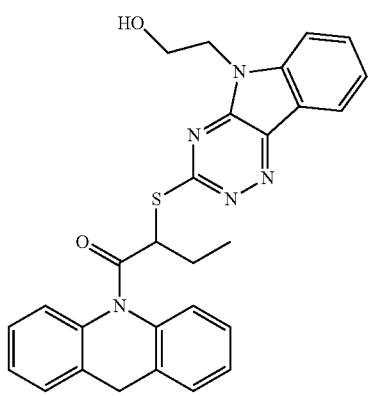 [SMILES: CCC(Sc1nnc2c3ccccc3n(CCO)c2n1)C(=O)N1c2ccccc2Cc2ccccc21]

or a pharmaceutically acceptable salt thereof. In another particular embodiment, the composition comprises a compound according to Formula (I), wherein G₂ is

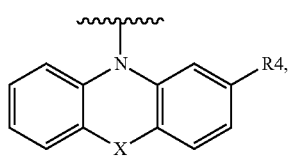

X is CH₂, R1 is CH₃CH₂, Y is H, R3 is H, and R4 is H. In still another particular embodiment, the composition comprises a compound according to Formula (I), wherein G₂ is

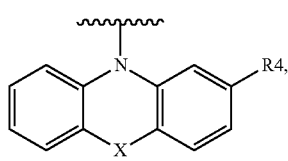

X is CH₂, Y is R2, R1 is CH₃CH₂, R2 is

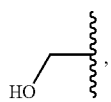

R3 is H, and R4 is H.

In another embodiment, of the present disclosure, a composition is provided, the composition comprising a compound according to Formula (I) or a pharmaceutically acceptable salt thereof, wherein, G₂ is:

X is: CH₂, O, or S;
R1 is: CH₃CH₂;
Y is: H;
R3 is H; and R4 is H, Cl, or OCH₃.

In another embodiment of the present disclosure, a composition is provided, the composition comprising a compound according to Formula (I) or a pharmaceutically acceptable salt thereof:
wherein, G₂ is:

X is: S;
R1 is: CH₃CH₂, or CH₃CH₂CH₂CH₂;
Y is: H;
R3 is H, OCH₃, an alkyl group, or a halogen;
R4 is H.

In another embodiment of the present disclosure, a composition is provided, the composition comprising a compound according to Formula (I) or a pharmaceutically acceptable salt thereof:
wherein G₂ is:

X is: S;
R1 is: CH₃CH₂;
Y is:

R3 is H;
R4 is H; and
R5 is:

In another embodiment of the present disclosure, a composition is provided, the composition comprising a compound according to Formula (I) or a pharmaceutically acceptable salt thereof:
wherein, G₂ is:

X is: S;
R1 is: CH₃CH₂;
Y is: R2;
R2 is:

-continued

[structure: phenethyl-triazole-CH2-]  , or

[structure: H3CH2CO-C(=O)-CH2CH2CH2-triazole-CH2-] ;

R3 is H; and
R4 is H.

According to another embodiment of the present disclosure, a composition is provided, the composition comprising a compound according to Formula (I) or a pharmaceutically acceptable salt thereof:

Formula (I)

[structure of Formula (I) with Y-N, R3, S, R1, G2, O]

wherein, G2 is:

[phenothiazine with X, R4] , [benzothiazine] ,

[tetrahydroquinoline] , [thiomorpholine] , or [dihydropyrrolopyridine] ;

X is: $CH_2$, O, NH, or S;
R1 is: $CH_3$, $CH_3CH_2$, $CH_3CH_2CH_2$, or $CH_3CH_2CH_2CH_2$;
Y is: H,

[structure: R5-C(=O)-CH-] , $CH_2CH_2OH$, $CH_2CH_2CCH$;

[structure: -CH2-C(=O)-OC2H5] ;

or R2;
R2 is:

[H3CH2CO-C(=O)-CH-] , [HO-C(=O)-CH-] , [HO-CH2-] , [HC≡C-CH-] ,

[HC≡C-CH2-CH-] , [Ph-C(=O)-CH-] ,

[phenethyl-triazole-CH-] ,

[phenethyl-triazole-CH2-] , or

[H3CH2CO-C(=O)-CH2CH2CH2-triazole-CH2-] ;

R3 is H, an alkyl group, OCH₃ or a halogen;
R4 is H, a halogen, or OCH₃; and
R5 is:

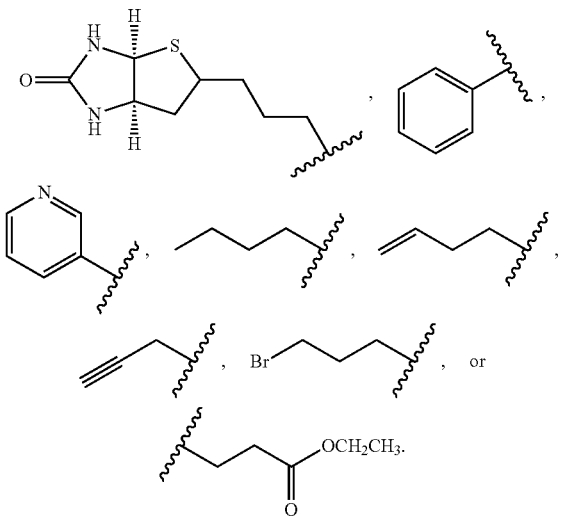

In another embodiment of the present disclosure, a composition is provided, the composition comprising a compound according to Formula (I) or a pharmaceutically acceptable salt thereof: wherein, $G_2$ is:

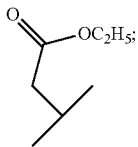

X is: $CH_2$;
R1 is: $CH_3CH_2$;
Y is: H, $CH_2CH_2OH$, $CH_2CH_2CCH$; or R2;
R2 is:

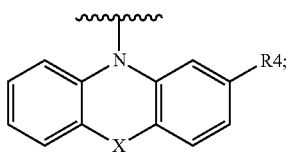

R3 is H, an alkyl group, OCH₃, or a halogen; and
R4 is H.

In another embodiment, a method of increasing apoptosis is provided, the method, comprising the steps of contacting at least one eukaryotic cell with an effective amount of any of the above compositions containing a compound according to Formula (I) or a pharmaceutically acceptable salt thereof.

In another embodiment, a method of treating a patient is provided, the method comprising the steps of administering at least one therapeutically effective dose of any of the above compositions containing compound according to Formula (I) or a pharmaceutically acceptable salt thereof to a human or to an animal. In a particular embodiment, the compound of Formula I is co-administered to said human or said animal along with a therapeutically effective dose of at least one chemotherapeutic agent. In another particular embodiment, the human is diagnosed with cancer. In another particular embodiment, the human is diagnosed with lung cancer. In another particular embodiment, the chemotherapeutic agent is selected from the group consisting of: cisplatin and doxorubicin.

BRIEF DESCRIPTION OF THE SCHEMES, FIGURES, AND TABLES

FIGS. 8A and 8B show the cellular activity of INZ analogs S1-S34. Initial Inauhzin analogs were purchased and tested the activity on H460 and HCT116$^{p53+/+}$ by IB. Cells were treated with the compounds at 2 μM or 20 μM for 18 hrs and harvested for IB and their p53 induction activity as quantified from IB data as shown in FIG. 8A-FIG. 8B.

FIGS. 9A and 9B show the cellular activities of INZ synthetic analogs 6-37. Cellular activity of INZ synthetic analogs 6-37 measured using IB that detects p53 levels and activity in H460 and HCT116 cells. FIG. 9A shows the results for cells that were harvested for IB with antibodies as indicated after being treated with each compound for 18 hrs as shown in representative blots (number denotes each compound; Inauhzin, INZ). FIG. 9B shows the p53 induction activity as quantified from IB data. 50 μg of total proteins was used per lane for the results shown in FIGS. 9A-9B.

Figure 10A:
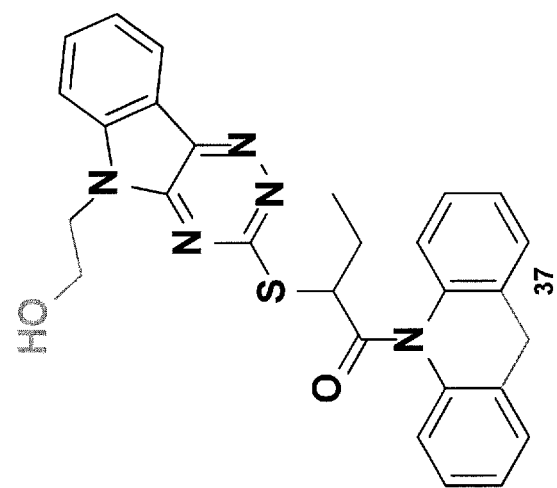

FIG. 10A illustrates the structure of INZ synthetic analog 37.

Figure 10B:
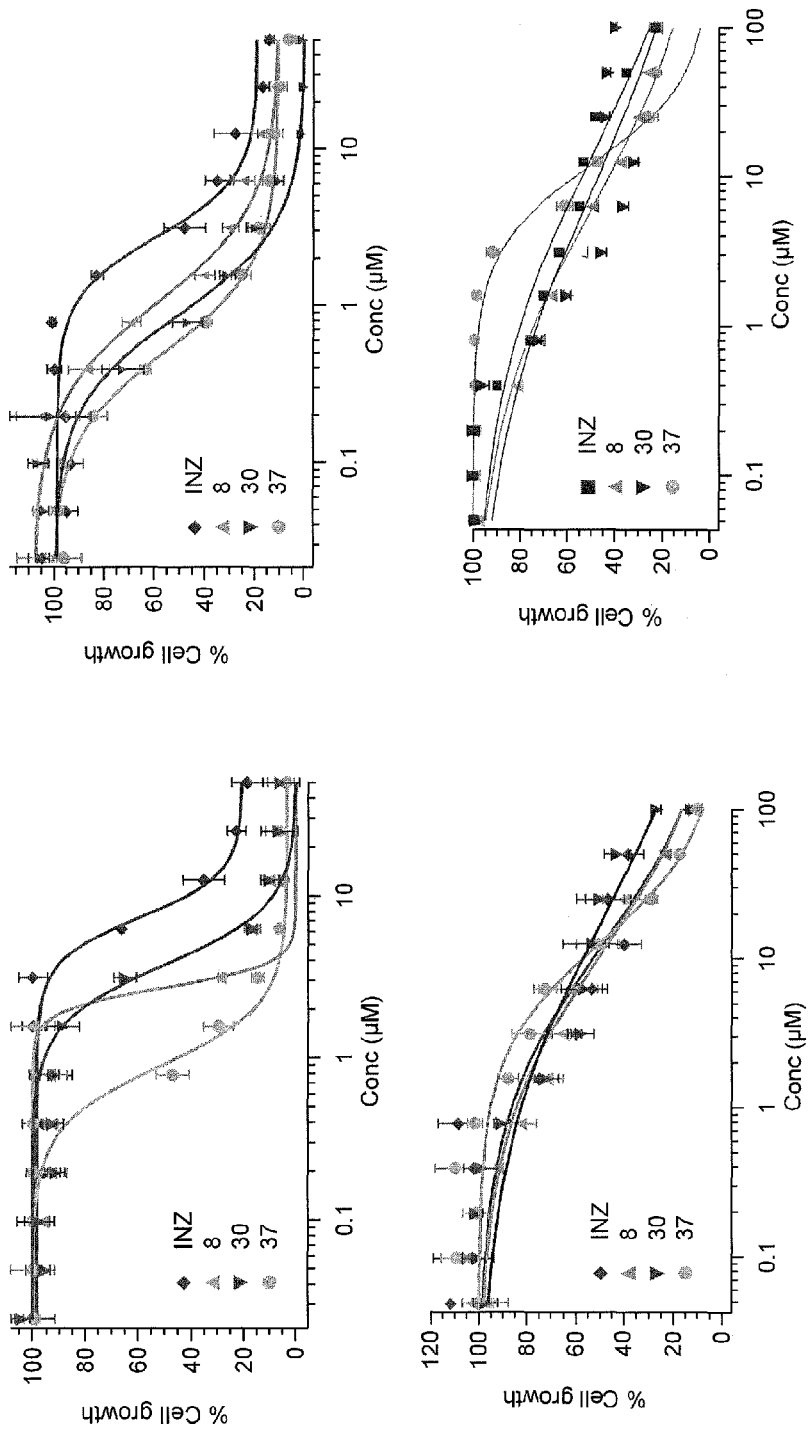

FIG. 10B shows the cell growth inhibition by selected INZ Synthetic Analogs. FIG. 10B shows representative cell growth inhibition curves of INZ synthetic analogs 8, 30 and 37 in H460 and HCT116 cell lines.

Figure 11:
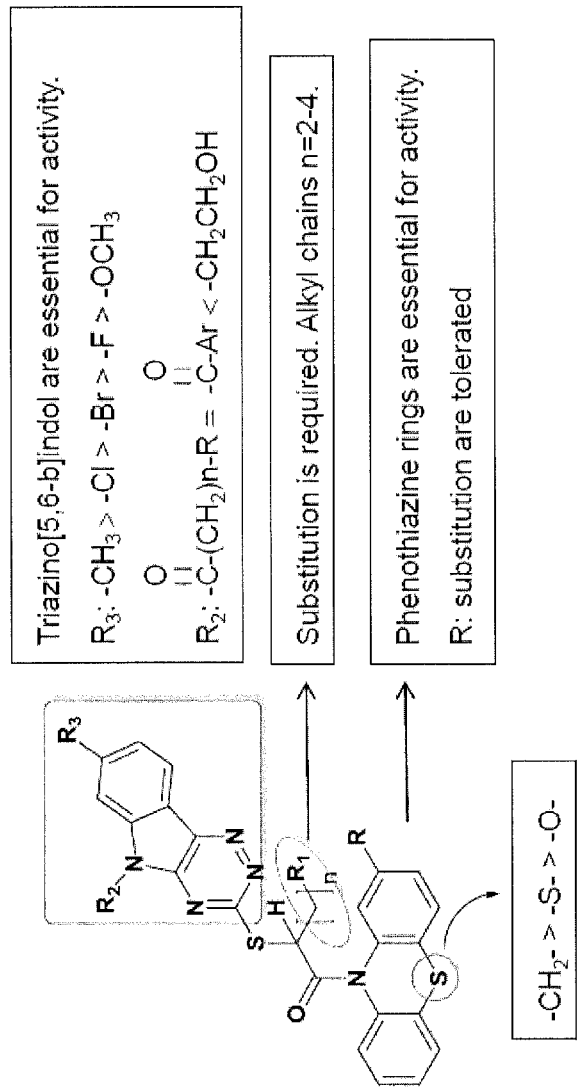

FIG. 11 illustrates a summary of some of the Structure-Activity Relationships between compounds related to INZ.

Figure 12A:
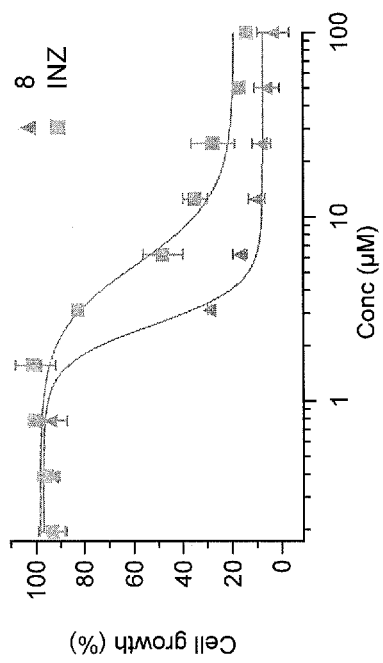
Figure 12B:
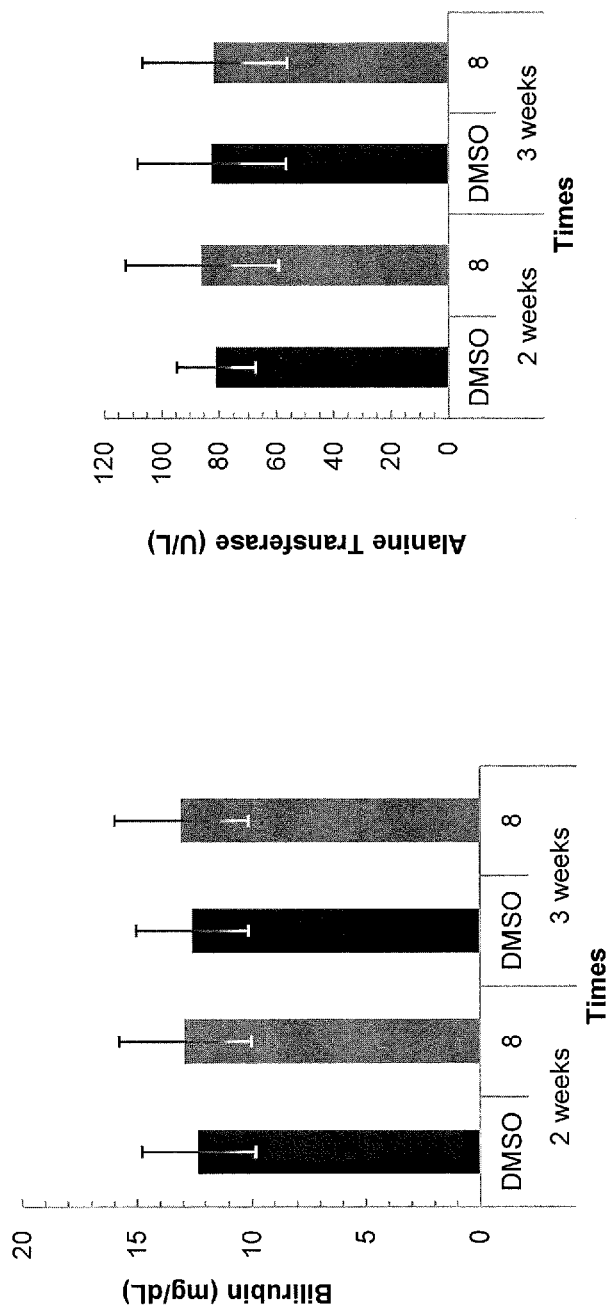

FIGS. 12A and 12B show the comparative potency of INZ and compound 37 and observed toxicity in cell based and in vivo biochemical toxicity assays. FIG. 12A shows the cell growth inhibition curves of INZ and compound 37 in H460 cells. $EC_{50}$ and $EC_{90}$ values represent the average of triplicates within 10% relative standard deviation. The results were repeated in two independent experiments. FIG. 12B shows assay results for Alanine transferase and total bilirubin. Compound 37 was administered i.p. at 50 mg/kg once per day for two weeks in C57BL/6 and their blood was collected for Alanine transferase and total bilirubin biochemical assay.

Figure 13A:
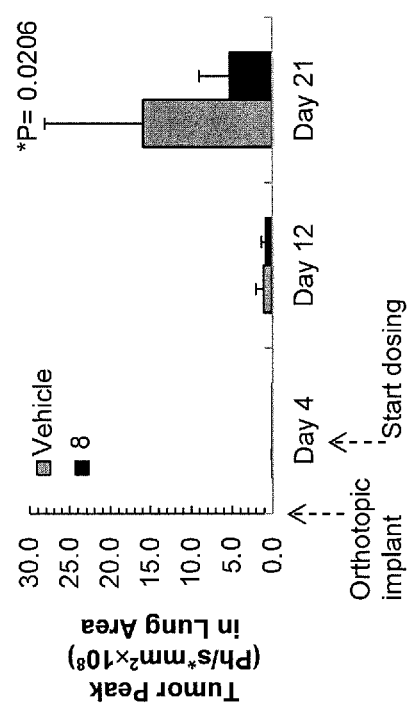
Figure 13B:
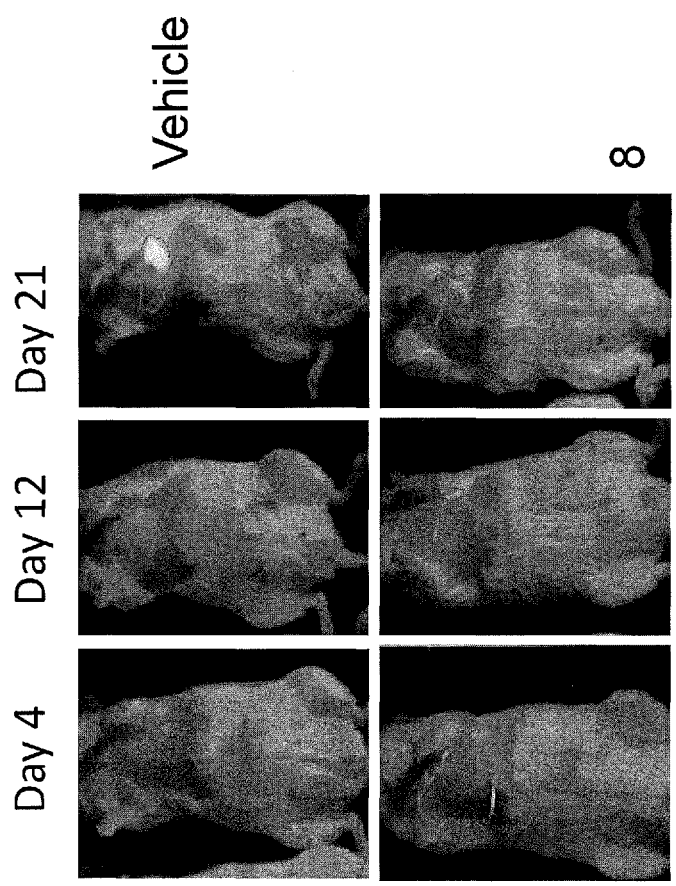

FIGS. 13A and 13B show the effects of compound 37 on the growth of H460 orthotopic lung tumors. Each mouse was dosed once a day via i.p. with either vehicle or compound 37 (50 mg/kg) for 3 weeks starting 4 days after implantation of 5×10⁵ H460-Luc tumor cells into the pleural space of the SCID mice. FIG. 13A shows the tumor burden in lung area measured by bioluminescent imaging (BLI) for each treatment group. Each value is a mean of five animals ±SD. FIG. 13B is bioluminescent imaging (BLI) of orthotopic lung tumors in SCID mice.

FIG. 14A illustrates the structure of INZ synthetic analog 38.

FIG. 14B illustrates the structure of INZ synthetic analog 39.

FIG. 14C illustrates the structure of INZ synthetic analog 40.

FIG. 14D illustrates the structure of INZ synthetic analog 41.

FIG. 14E illustrates the structure of INZ synthetic analog 42.

FIG. 14F illustrates the structure of INZ synthetic analog 43.

Figure 15A:
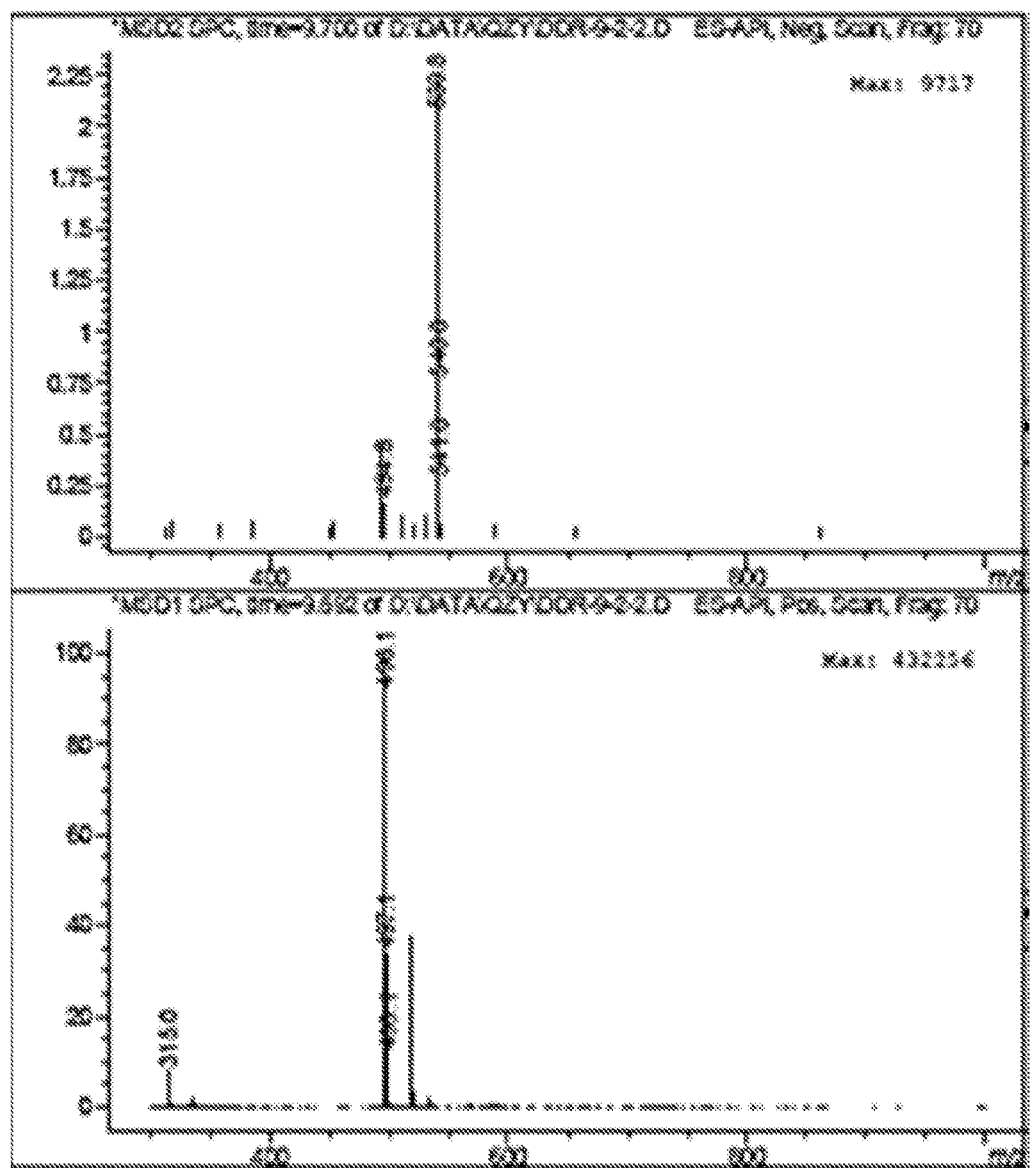

FIG. 15A shows mass spectrometry characterization data for INZ synthetic analog 42.

Figure 15B:
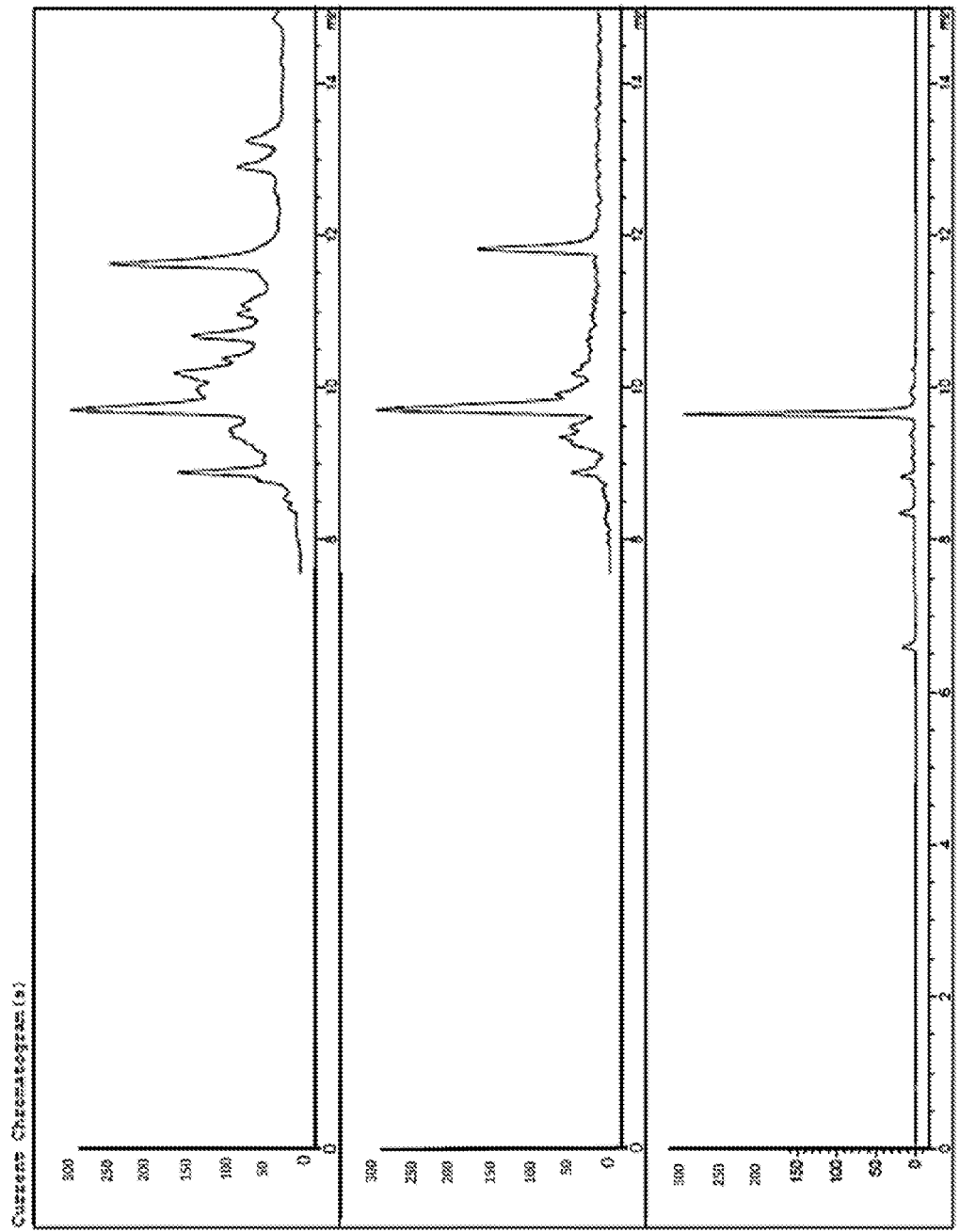

FIG. 15B shows liquid chromatography characterization data for INZ synthetic analog 42.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the terms 'therapeutically effective dose,' 'therapeutically effective amounts,' and the like, refers to a portion of a compound that has a net positive effect on the health and well being of a human or other animal. Therapeutic effects may include an improvement in longevity, quality of life and the like these effects also may also include a reduced susceptibility to developing disease or deteriorating health or well being. The effects may be immediately realized after a single dose and/or treatment or they may be cumulatively realized after a series of doses and/or treatments.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For addition information on some pharmaceutically acceptable salts that can be used to practice the invention please reviews such as Berge, et al., 66 J. PHARM. SCI. 1-19 (1977), Haynes, et al, J. Pharma. Sci., Vol. 94, No. 10, October 2005, pgs. 2111-2120, the disclosures of which are hereby incorporated by reference in their entirety, and the like.

Design and Chemical Synthesis

Figure 1:
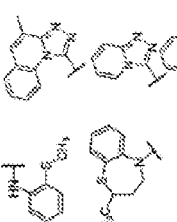
FIG. 1 illustrates chemical structures of representative commercial analogs S1-S34.
Figure 2:
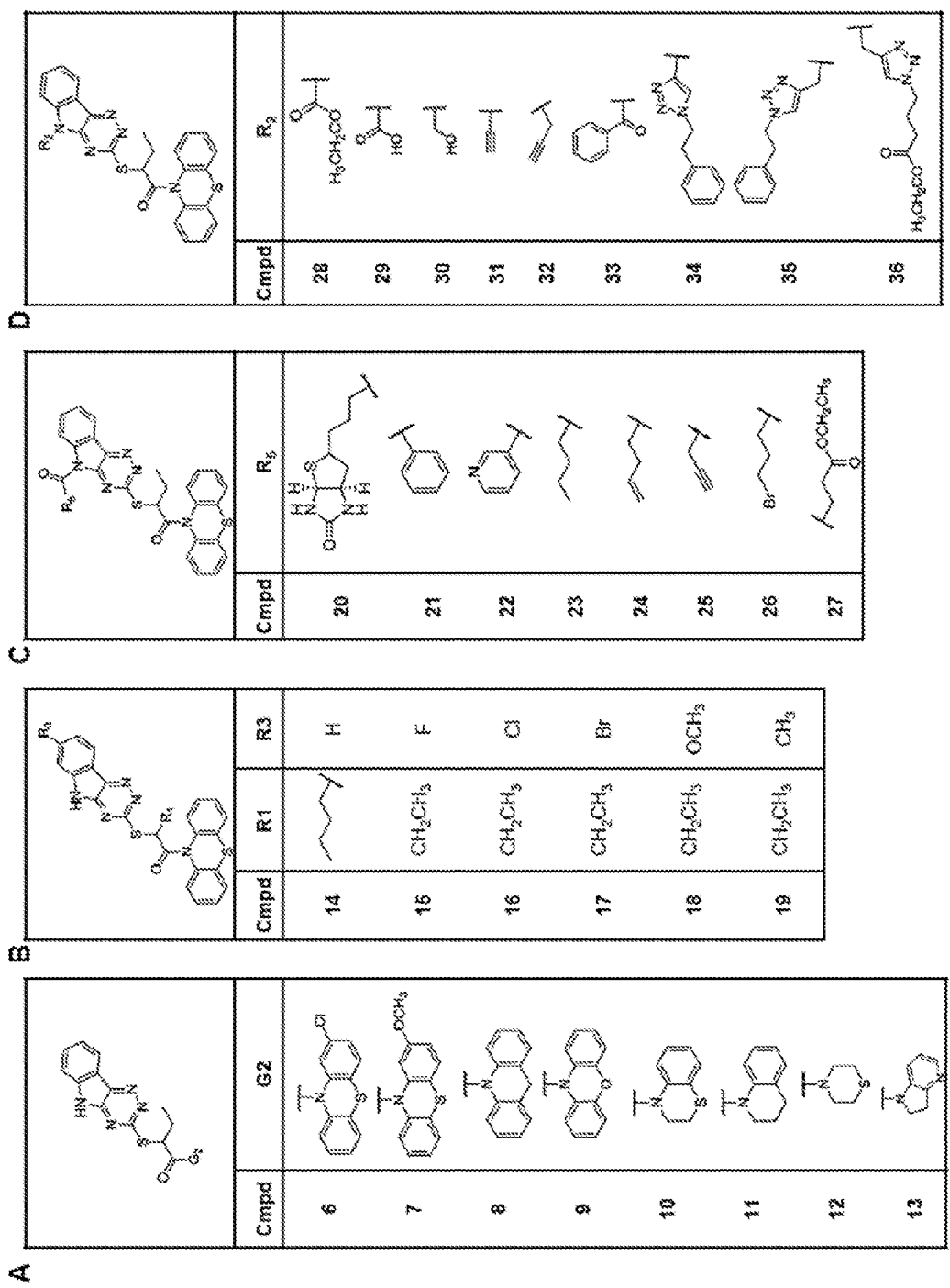
FIGS. 2A-2D illustrate chemical structures of INZ synthetic analogs 6-36.
Figure 7:
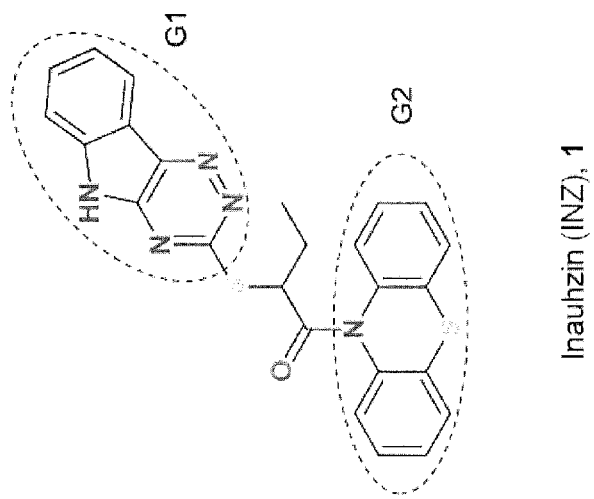
FIG. 7 illustrates the structure of Inauhzin (INZ).
Figure 8:
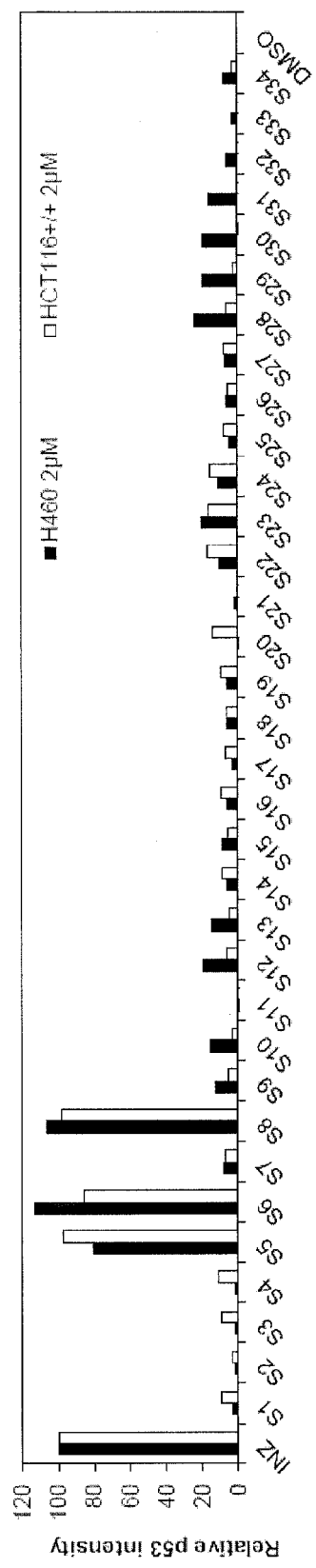
Figure 8:
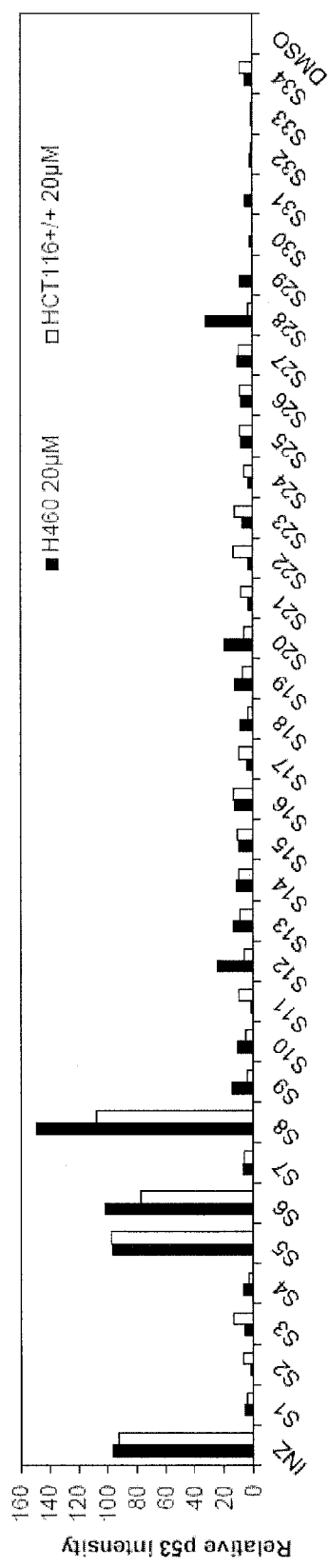

Structurally, INZ (1) possesses two distinct chemical components: triazino[5,6-b]indol (G1) and phenothiazine (G2) moiety (FIG. 7). Preliminary SAR studies were performed using 46 purchased analogous of INZ with diversities at G1 and G2. This study also investigated the activity of the compounds in cell-based assays for their ability to induce p53 levels in p53 containing human colon cancer HCT116$^{+/+}$ cells and/or human lung cancer H460 cells using immunoblotting (IB) (FIG. 1 and FIG. 8). The results indicated that a unique structure scaffold might be required for the activity of INZ in cells. Removal of the ethyl group at R1 (S1-S3) or modification at both $R_2$ and $R_3$ positions on the indol moiety of INZ (S4) disabled the compound's ability to activate p53 in cells (FIG. 8). Apparently, the $R_2$ position can be modified and substituted without loss of activity by replacing it with some alkyl groups, such as methyl, ethyl and allyl, but not propyl (S5-S8). Both triazino [5,6-b]indol (G1) and phenothiazine (G2) are essential functional groups for p53 induction. INZ analogs that included ethyl groups at the $R_1$ position but lacked either functional groups G1 (S9-S10), or G2 (S19-S22) failed to induce p53. Compounds S11-S18, S23-S28, and S29-S34 with substituted aromatic moieties other than triazino[5,6-b]indol at G1 and/or phenothiazine at G2 had very low or no activity. Overall, the results suggest that a specific chemical structure with the intact triazino[5,6-b]indol-3-ylthio)butanoyl]-10H-phenothiazine might be crucial for p53 activation in cells. Indeed, INZ (1) displayed more potent p53 activation and anticancer inhibition than either of its component fragments, compound 2' or 3' (Scheme 2, FIG. 4, and data not shown). These results suggest that a synergism is achieved when these two structural units are combined within a single molecule. Therefore, further attention was focused on the structural modifications of the pharmacologically active core: triazino[5,6-b]indol or phenothiazine. Modifications included extension of carbon chain length on R1 (14) (FIG. 2B), the substitution on the phenothiazine ring (G2) (6-13) (FIG. 2A) or on the triazino[5,6-b]indol ring (G1) (15-36) (FIGS. 2B-2D).

The syntheses of these INZ derivatives are outlined in Schemes 1, 2, 3, and 4 (FIGS. 3-6).

Figure 3:
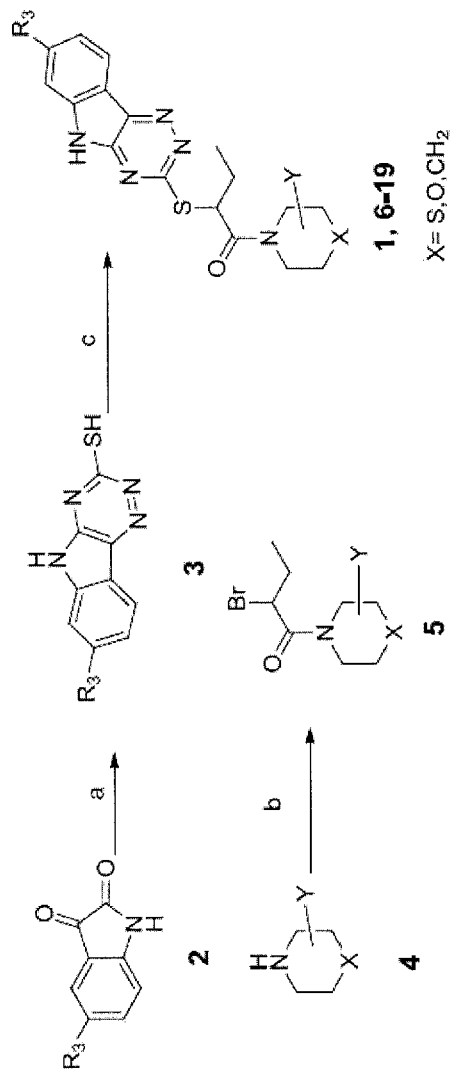
FIG. 3 illustrates the scheme 1 synthesis of INZ analogs 6-19.

The synthesis of compounds INZ (1) and 6-19 is outlined as Scheme 1 (FIG. 3). The 5H-[1,2,4]triazino[5,6-b]indole-3-thiol 3 was prepared from the commercial isatin according to the standard procedure. The bromide 5 was synthesized through refluxed thiophenol with the bromobutyryl bromide in toluene. Then the thiol 3 was reacted with bromide 5 in the presence of Et$_3$N and afforded compound 1, and 6-19. Other bases were tested and some byproducts were produced, which gave rise to low yields.

Figure 4:
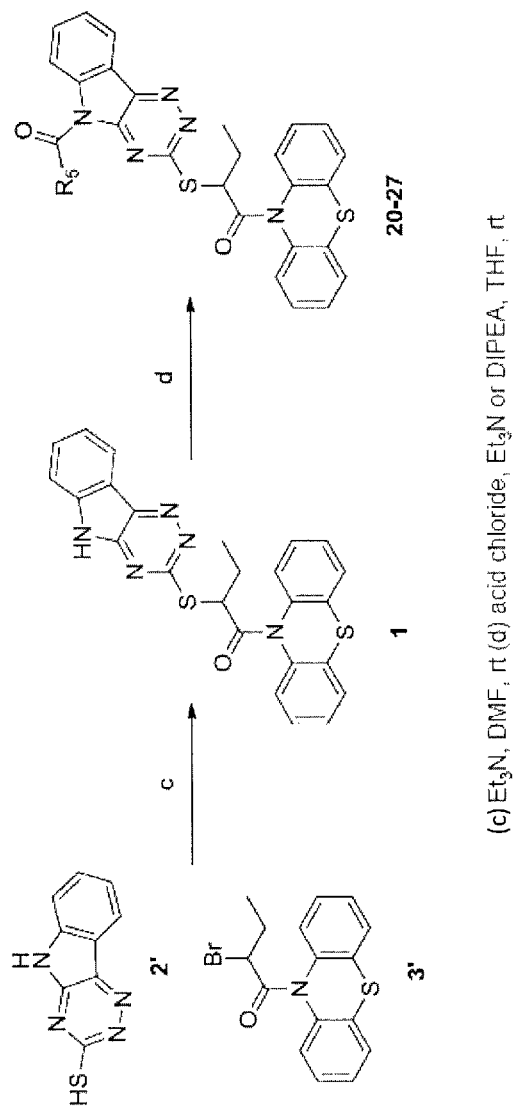
FIG. 4 illustrates the scheme 2 synthesis of INZ analogs 20-27.

The amide derivatives 20-27 were prepared in one step from INZ (1) in the presence of organic bases as depicted in Scheme 2 (FIG. 4).

Figure 5:
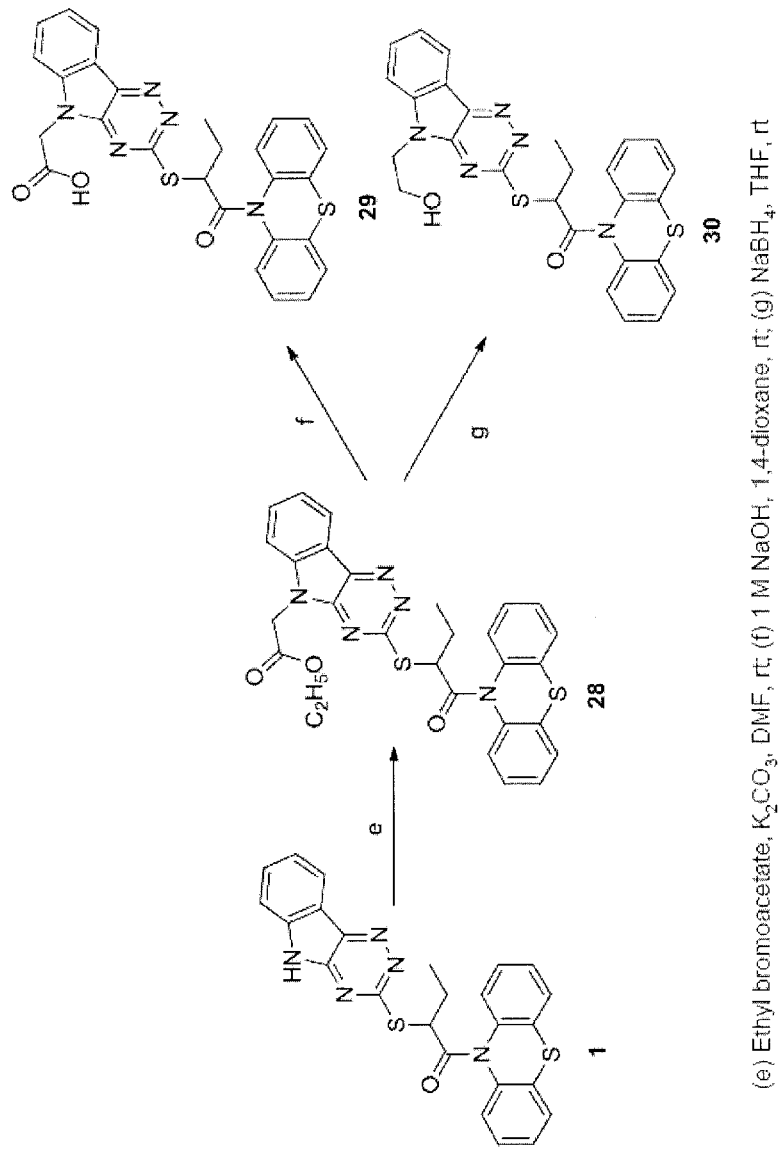
FIG. 5 illustrates the scheme 3 synthesis of INZ analogs 28-30.
Figure 6:
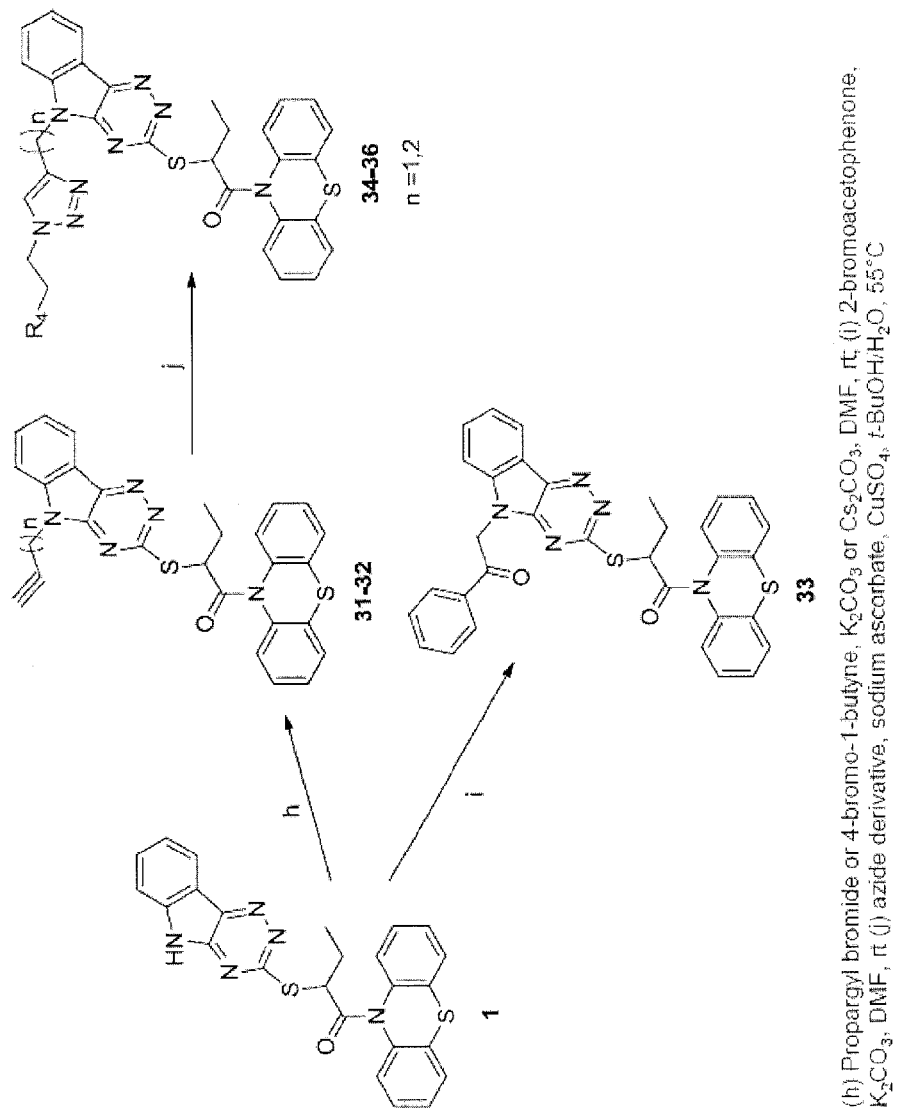
FIG. 6 illustrates the scheme 4 synthesis of INZ analogs 31-36.

The amine derivative 28 was synthesized from INZ (1) and ethyl bromoacetate in the presence of K$_2$CO$_3$, which was depicted in Scheme 3 (FIG. 5). Other organic bases, such as Et$_3$N or DIPEA, were tested and the reaction proceeded very slowly with low yields. Compound 28 was hydrolyzed by 1 M NaOH and afforded the acid 29. The alcohol 30 was obtained through reduction of 28 by NaBH$_4$.

LiBH$_4$ was tested and several byproducts were produced as revealed by TLC analysis. Scheme 4 (FIG. 6) shows the "click chemistry" for the synthesis of triazol derivatives. Triazols 34-36 were obtained in good yields through the reaction of azide derivative and the propargyl 31 and 32 under the standard conditions.

Biological Assessments of INZ Analogs

Figure 9:
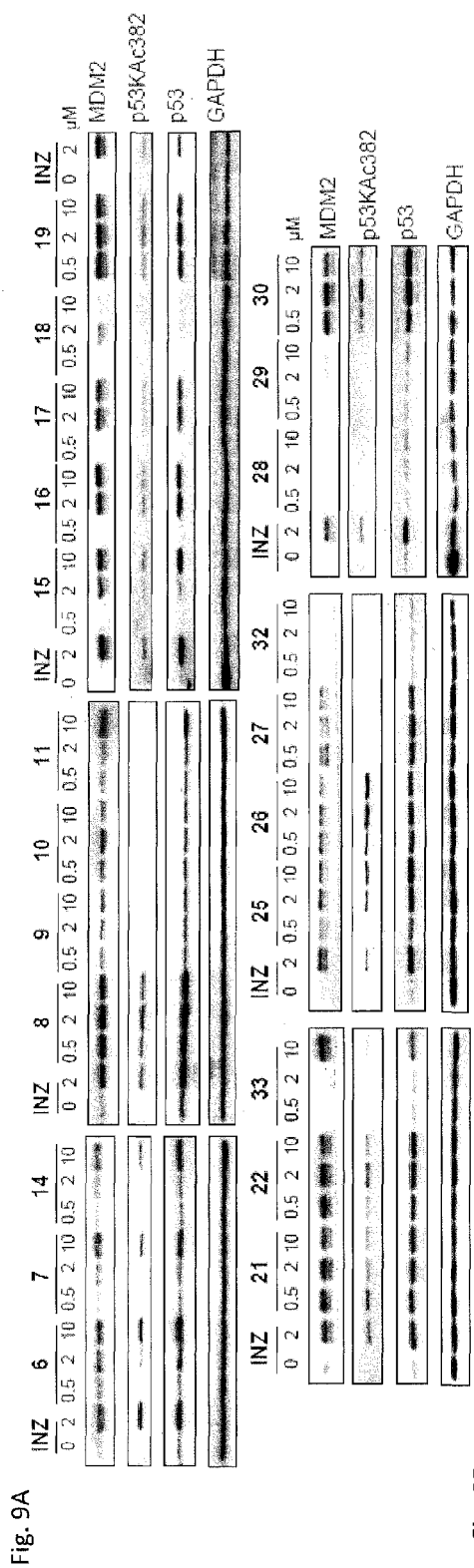
Figure 9:
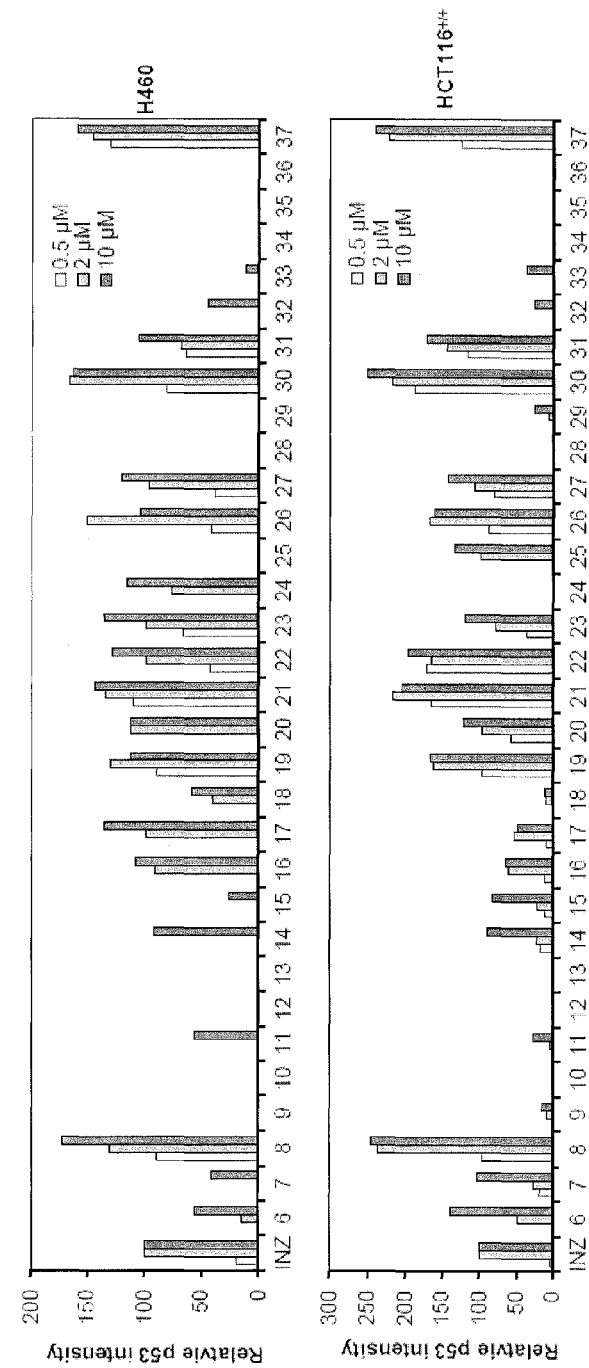

The synthetic analogs were then assayed for their potential to induce p53 level and activity in H460 cells and HCT116$^{+/+}$ cells by IB. Compounds were added into cultured H460 and HCT116$^{+/+}$ cells at 0.5, 2, 10 µM for 18 hrs and harvested for IB. The p53 activation was assessed by up-regulating the levels of MDM2, p53 and p53 acetylation. The induction level of p53 by each of the tested INZ analogs was normalized against the loading control of GAPDH and compared to the level of p53 in the cells treated with 2 µM INZ (FIG. 9). Compounds showing good efficacy in p53 induction were further subjected to a 3-day WST assay to assess their ability to kill cancer cells. INZ was used along with the analogs as a positive control in each assay. The EC$_{50}$ values for their ability to inhibit cell growth were calculated through serial dilution of their concentrations with the highest concentration at 50 µM. Four-parameter or two-parameter Hill equation was employed to calculate and plot the dose-response curves as shown with some representative compounds in FIG. 10 and Table 1.

potency than did INZ in its inhibitory effect on H460 (EC$_{50}$=2.7 µM) (FIG. 10) and HCT116$^{+/+}$ cells (EC$_{50}$=1.3 µM) (FIG. 10). The EC$_{90}$ values of this analog were in the range of 3.5-10 µM, which were 3-10 fold lower than those for INZ.

Compound 14 (FIG. 2B) with the longer chain containing butyl at R1 position exhibited lower activity for p53 induction, which further indicated that the appropriate length of alkyl chain at R1 position is crucial for the activity of INZ, as INZ activity in p53 activation was reduced or lost when the chain was either longer than 2 carbons (14, FIG. 2B) or removed (S2-S3, FIG. 1). Compounds 15-19 (FIG. 2B) were synthesized to determine the effect of different substituents, such as electron-withdrawing group (halogen atoms) and electron donating group (methyl or methoxy), at R$_3$ position of indole ring (G1) on p53 induction. Compounds 16 and 17, which have a chlorine and bromine atom, respectively, exhibited similar activity to that of INZ in HCT116$^{+/+}$ cells with a dose-dependent induction of p53 acetylation at lysine 382, p53 protein level and the up-regulation of MDM2 level. Compound 18 with a methoxy group displayed a marked decrease in p53 activation. In contrast, the methyl derivative 19 exhibited a significant effect on p53 induction compared to INZ at 0.5 µM. It also inhibited the proliferation of H460 and HCT116$^{+/+}$ with EC$_{90}$ values of ~20-30 µM, which were 1.5 fold lower than that for INZ (FIG. 10C). These results

TABLE 1

DOSE-RESPONSE DATA FOR SELECTED COMOUNDS

| | Cancer cells | | | | | | | | Normal cells | |
|---|---|---|---|---|---|---|---|---|---|---|
| | H460 p53 wild type | | HCT116$^{+/+}$ p53 wild type | | H1299 p53 null | | HCT116$^{-/-}$ p53 null | | WI-38 p53 wild type | |
| | $^a$EC$_{50}$ (µM) | $^b$EC$_{90}$ (µM) | EC$_{50}$ (µM) | EC$_{90}$ (µM) | EC$_{50}$ (µM) | EC$_{90}$ (µM) | EC$_{50}$ (µM) | EC$_{90}$ (µM) | EC$_{50}$ (µM) | EC$_{90}$ (µM) |
| 8 | 2.7 ± 0.3 | 3.5 | 1.3 ± 0.3 | 10.0 | 10.4 ± 1.6 | 223.9 | 5.9 ± 1.0 | 240.9 | $^c$n.d. | |
| 19 | 6.0 ± 0.6 | 26.5 | 2.2 ± 0.2 | 29.7 | 40.2 ± 7.4 | 172.8 | 44.2 ± 10.3 | >1000 | n.d. | |
| 20 | 2.9 ± 0.2 | 7.5 | 2.5 ± 0.6 | 18.3 | | | | | | |
| 21 | 4.3 ± 0.3 | 9.6 | 2.1 ± 1.0 | 21.9 | 12.6 ± 1.4 | 82.3 | 28.2 ± 1.4 | >1000 | | |
| 22 | 4.9 ± 1.0 | 20.5 | | | | | | | | |
| 23 | 6.7 ± 0.7 | 22.6 | | | | | | | | |
| 24 | 5.7 ± 0.3 | 14.5 | | | | | | | | |
| 26 | 16.0 ± 0.9 | 38.2 | | | | | | | | |
| 27 | 3.4 ± 0.3 | 9.0 | | | | | | | | |
| 30$^a$ | 3.5 ± 0.4 | 7.7 | 0.8 ± 0.5 | 4.6 | 16.6 ± 4.1 | 921.6 | 7.8 ± 3.4 | 741.8 | n.d. | |
| 37$^b$ | 0.7 ± 0.1 | 3.6 | 0.5 ± 0.1 | 5.0 | 11.2 ± 3.5 | 58.9 | 12.8 ± 1.7 | 91.7 | n.d. | |
| INZ | 7.7 ± 1.1 | 39.9 | 2.7 ± 0.3 | 30.5 | 11.6 ± 3.4 | 217.4 | 13.3 ± 2.4 | 212.6 | n.d. | |

$^a$EC50 of the selected INZ analogs represent the average of triplicates. The EC50 values were determined by the two-parameter Hill equation where EC50 and the Hill coefficient were allowed to refine while the maximal and minimal values remain fixed.
$^b$EC$_{90}$ values were calculated from the EC$_{50}$ and Hill slope by a web-based calculator: http://www.graphpad.com/quickcalcs/Ecanything1.cfm.
$^c$Not able to be determined.

Anti-Proliferative Effect of Synthetic INZ Analogs

In synthetic INZ analogs containing triazino[5,6-b]indol (G1), subtle and major modifications to phenothiazine ring (G2) generally led to less potent molecules. Though subtle changes on the branches of the phenothiazine ring were tolerated (for instance, compounds 6 and 7 with chlorine or methoxy remained active in p53 induction) (FIGS. 2A and 9), they did not reach 50% p53 induction in H460 cells at 2 µM. The removal of any ring of G2, as shown for compound 10-13 (FIG. 2A), caused loss of activity, and those compounds were essentially inactive (FIG. 9). The exception to this trend was substitution of the sulfur atom with methylene (8). 1-acridin-INZ derivative (8) drastically induced p53 at 0.5 µM, whereas compound 9, whose sulfur was substituted with oxygen, was inactive (FIG. 9). It should be noted that 1-acridin-INZ (8) also exhibited more than 2 fold higher indicate that the order of influence of these substituents on the antiproliferative activity of INZ is as follows: CH$_3$>Cl=Br>F>OCH$_3$.

The results from preliminary biological screening of INZ analogs (S5-S8, FIG. 1) suggested that R$_2$ position could be modified. Biotin was conjugated directly to INZ through the formation of the amide bond at the active hydrogen of R$_2$ in order to form compound 20 (FIG. 2C). This biotin-conjugated INZ was initially designed for target identification studies. Surprisingly, biotinylated INZ (20) was as effective as INZ in the induction of p53 acetylation and level in both H460 and HCT116$^{+/+}$ cells (FIG. 9B). Another biotin-conjugated compound derived from the inactive compound 15 was used as a negative control in the target identification screening (data not shown). In addition to compound 20, some other amide compounds (21-27) (FIG. 2C) were made through the same procedure. All these compounds with various aldehyde substitutions on $R_2$ exhibited good activities in p53 induction and cell growth inhibition in comparison with INZ (FIGS. 9-10). Derivatives 20, 21 and 27 showed similar $EC_{90}$ values of 7.5, 9.6 and 9.0 μM, respectively whereas INZ is about 39.9 μM. Removal (25→32, FIGS. 2C-2D) or separation (21→33, FIGS. 2C-2D) of electron-withdrawing aldehyde atom from the indol resulted in a significant decrease in activity (FIG. 9). Replacing the aldehyde with an ester group (28) or carboxylic acid (29) resulted in essentially inactive analogs, in striking contrast to its alcohol derivative 30, which was comparable to compound 8 in p53 activation and cell growth inhibition (FIG. 2D, 10-11). The $EC_{90}$ values of compound 30 as tested in H460 and HCT116$^{+/+}$ cells, respectively, were ~7.7 μM and 4.6 μM, which was 5 fold lower than that of INZ (FIG. 10). Since compounds 8 and 30 displayed more potent activity compared than did INZ, the analog 37 which includes both substitution of the sulfur atom with methylene on G2 and alcohol substitution on G1 was synthesized. Remarkably, compound 37 was 10- and 5-fold more active than was INZ in growth inhibition of H460 and HCT116$^{+/+}$ cells ($EC_{50}$=0.7 μM and 0.5 μM), respectively.

INZ displayed much higher toxicity to p53-containing human cancer cells than to p53-null cancer cells. This was evident in the $EC_{50}$ and $EC_{90}$ values for the compounds, which were 1.5 and 5-7 fold greater in p53-null cells than in p53-containing cell lines, respectively (FIG. 10C). The activity of INZ synthetic analogs was examined further by conducting in vitro cytotoxicity assays using p53 null lung cancer H1299 cells and colon cancer HCT116$^{-/-}$ cells. Compounds 8, 19, 21, 30 and 37 were much less effective in H1299 cells and HCT116$^{-/-}$ cells, in contrast to their inhibitory activity against p53-containing cells (FIG. 10C); the $EC_{50}$ values of compounds 8, 30 and 37 on H1299 were 10.4, 16.6 and 11.2 μM, respectively, which were 3-15 fold higher than those measured using H460 cells. The $EC_{90}$ values of compound 8, 30 and 37 on H1299 cells and HCT116$^{-/-}$ cells were greater than 50 μM whereas those on H460 and HCT116$^{+/+}$ cells were 3.5 and 10, 7.7 and 4.6, and 3.6 and 5.0 μM, respectively. Remarkably, these synthetic analogs were much less toxic to normal human fiberbrast cell WI-38 (FIG. 10), while they were much more potent than was INZ in killing p53-containing cancer cells. For example, the $EC_{50}$ value of compound 37 for WI-38 could not be determined at the highest concentration tested (50 μM) in comparison of its $EC_{50}$ values of 0.7 and 0.5 μM to p53-containing H460 and HCT116$^{+/+}$ cells, respectively. Together, these results indicate that these more potent INZ analogs, such as compounds 8, 30 and 37, possess strong p53-dependent cytotoxicity. Among them, compound 37 stands out as the most effective INZ analog identified in this study.

Initial studies on the 46 commercial analogs of INZ yielded information on the important functional groups at each of its two scaffolds identified as triazino[5,6-b]indol ring (G1) and phenothiazine ring (G2). The functional analyses of the commercial and synthetic analogs of INZ and their ability to activate p53 and to inhibit cell growth further as described above validates that each of the functional groups of INZs is critical for p53 activation and inhibition of cancer cell growth (FIG. 11). Most modifications to phenothiazine ring G2, such as the branch substitutions (6-7, 9), or replacement with other rings (10-13, S19-S22), led to decreased activity in p53 induction, with the apparent exception that the substitution of sulfur in the G2 region by methylene (1→8) showed greater potency than compound 1 in both p53 induction and cancer cell inhibition. Analyses of analogs S1-S3, and 14 demonstrate that the ethyl group at $R_1$ is likely to be required for the activity of these compounds. The butyl group was tolerated. Modification of $R_3$ position at the region G1 with methyl, but not halide ormethoxy substitutions, increased activity in both of the assays (15-19). Most modifications on $R_2$ at the G1 region resulted in the impressive improvement in terms of p53 activation compared to compound 1 (20-27, 30-31). Overall, the best compound from this study was 1-acridin-INZ alcohol (37). The potency of this analog, compared to INZ, was improved nearly 5- to 10-fold in cancer growth inhibition. Interestingly and importantly, compounds 8, 30 and 37 were more potent in p53 activation than their parental compound INZ especially with the selective toxicity to p53-containing tumor cells, but not to normal cells.

Based on these SAR and cell-based analyses, 1-acridin-INZ alcohol (37) represented a candidate for further characterization of its biological activity against cancer by using orthotopic lung tumors derived from H460 cells (See FIGS. 12-13).

EXPERIMENTAL SECTION

Compounds S1-S34. INZ analogs S1-S34 were purchased from Asinex, ChemDiv and ChemBridge. Compounds S1-S5 were described in a preceding paper, re-validated by LC/MS on an Agilent 1200 LC/MS system (Agilent Technology) at the Chemical Genomics Core Facility of Indiana University School of Medicine. The minimum purity of all compounds is higher than 90%.

Cell Culture and Immunoblotting Analysis. Human lung carcinoma H460, non-small-cell lung cancer H1299, human colon cancer HCT116 (HCT116$^{+/+}$), and human embryonic fibroblast WI-38 were bought from the American Type Culture Collection (ATCC). Human colon cancer HCT116 p53 null cell lines (HCT116$^{-/-}$) were generously offered by Dr. Bert Vogelstein (Johns Hopkins University). Those cell lines were cultured in Dulbecco's modified Eagle's medium supplemented with 10% fetal bovine serum, 100 U per mL penicillin, and 100 U per mL streptomycin. Compounds were dissolved in DMSO and diluted directly into the medium to the indicated concentrations; 0.1% DMSO was used as a control. After incubation with the compounds for 18 h, cells were harvested and lysed in 50 mM Tris-HCl pH 8.0, 150 mM NaCl, 5 mM EDTA, 0.5% NP-40 supplemented with 1 mM DTT and 0.2 mM PMSF. An equal amount of protein samples (50 μg) was subjected to SDS-PAGE and transferred to a PVDF membrane (PALL Life Science). The membranes with transferred proteins were blocked with 1xTBST containing 5% non-fat, dried milk for 1 h at room temperature, and then incubated with anti-p53-acetylated (lys382, Cell Signaling), anti-p53 (mouse monoclonal, DO-1, Santa Cruz), anti-MDM2 (4B11)[14], or anti-GAPDH antibodies (Sigma) followed by a secondary antibody labeled with horseradish peroxidase (Pierce). The blots were developed by an enhanced chemiluminescence detection kit (Thermo Scientific), and signals were visualized by Omega 12iC Molcular Image System (UltraLUM).

Cell Viability Assay. To assess cell growth, the cell counting kit (Dojindo Molecular Technologies Inc., Gaithersburg, Md.) was used according to manufacturer's instructions. Cell suspensions were seeded at 3,000 cells per well in 96-well culture plates and incubated overnight at 37° C. Compounds were added into the plates and incubated at 37° C. for 72 hrs. Cell growth inhibition was determined by adding WST-8 at a final concentration of 10% to each well, and the absorbance of the samples was measured at 450 nm using a Microplate Reader (Molecular Device, SpecrtaMax M5$^e$). $EC_{50}$ values were determined by the Hill equation using Igor 4.01 (Lake Oswego, Oreg., USA).

General chemistry. All purchased chemicals were reagent-grade or better. Proton and carbon NMR spectra were recorded on a 500 MHz Bruker Avance II spectrometer. Chemical shifts are reported in δ (parts per million, ppm) with the δ 7.26 signal of $CDCl_3$ ($^1$HNMR), δ 2.50 signal of DMSO-$d_6$ ($^1$H NMR), or δ 77.2 signal of $CDCl_3$ ($^{13}$C NMR) as internal standards. All column chromatography was performed using Dynamic Adsorbents 230-400 mesh silica gel ($SiO_2$) with the indicated solvent system unless otherwise noted. TLC analysis was performed using 254 nm glass-backed plates and visualized using UV light (254 nm). HRMS data were obtained at the Mass Spectrometry Facility at IUPUI Chemistry Department on a Waters/Macromass LCT. All the synthetic compounds were analyzed by LC/MS on an Agilent 1200 LC/MS system (Agilent Technology) at the Chemical Genomics Core Facility of Indiana University School of Medicine and the purity was over 95%.

General Procedure for Synthesis of Compounds 1, 6-19

2-((5H-[1,2,4]triazino[5,6-b]indole-3yl)thio)-1-(10H-phenothiazin-10-yl)butan-1-one (1, INZ): 2-bromo-1-(10H-phenothiazin-10-yl)butan-1-one (3.675 g, 25 mmol) and 5H-[1,2,4]triazino[5,6-b]indole-3-thiol (2.125 g, 25 mmol) were dissolved in 50 ml anhydrous DMF and cooled to 0° C. 11.1 ml $Et_3N$ (250 mmol) was dropped to the above mixture. After stirring for 1.5h, TLC indicated that the reaction was completed and stopped. 300 ml ethyl acetate was added to the reaction mixture. The organic phase was washed by saturated $NH_4Cl$ for five times. It was dried by anhydrous $Na_2SO_4$ and filtered. The organic phase was concentrated to about 15 ml and the pale solid was formed. The amorphous solid was collected and washed by a few ethyl acetate. $^1$H NMR (500 MHz, DMSO-$d_6$) δ; 12.63 (br, 1H), 8.34 (d, J=7.5?, 1H), 7.89-7.96 (m, 1H), 7.56-7.73 (m, 4H), 7.37-7.47 (m, 5H), 7.29-7.22 (m, 1H), 5.27 (t, J=7.0, 1H), 1.86 (br, 1H), 1.74 (br, 1H), 0.85 (br, 3H). $^{13}$C NMR (125 MHz, DMSO-$d_6$) δ 170.0, 146.8, 141.7, 140.9, 138.5, 138.3, 131.4, 128.6, 128.2, 128.0, 127.7, 127.4, 123.0, 122.0, 118.0, 113.2, 31.1, 25.9, 11.8. HRMS was calculated for $C_{25}H_{19}N_5OS_2$ 469.1031 and found 469.1047.

2-((5H-[1,2,4]triazino[5,6-b]indol-3-yl)thio)-1-(2-chloro-10H-phenothiazin-10-yl)butan-1-one (6): Compound 6 was synthesized similarly to 1. $^1$H NMR (500 MHz, DMSO-$d_6$) δ 12.64 (d, J=17.5, 1H), 8.33-8.35 (m, 1H), 7.84-7.91 (m, 1H), 7.60-7.34 (m, 4H), 7.39-7.48 (m, 5H), 5.15-5.26 (m, 1H), 1.82 (br, 1H), 1.73 (br, 1H), 0.85 (br, 3H). HRMS calcd for $C_{25}H_{18}ClN_5OS_2$ 503.0641; found 503.0643.

2-((5H-[1,2,4]triazino[5,6-b]indol-3-yl)thio)-1-(2-methoxy-10H-phenothiazin-10-yl)butan-1-one (7): Compound 7 was synthesized similarly to 1. $^1$H NMR (500 MHz, DMSO-$d_6$) δ 12.65 (d, J=22.5, 1H), 8.32-8.35 (m, 1H), 7.59-7.73 (m, 1H), 7.36-7.53 (m, 7H), 7.21 (br, 1H), 6.96-7.21 (m, 1H), 5.29 (t, J=7.0, 1H), 3.51-3.71 (m, 3H), 1.95 (br, 1H), 1.77 (br, 1H), 0.86 (br, 3H). HRMS calcd for $C_{26}H_{21}N_5O_2S_2$ 499.1137; found 499.1144.

2-((5H-[1,2,4]triazino[5,6-b]indol-3-yl)thio)-1-(acridin-10(9H)-yl)butan-1-one (8): Compound 8 was synthesized similarly to 1. $^1$H NMR (500 MHz, DMSO-$d_6$) δ 12.60 (br, 1H), 8.32 (d, J=7.5, 1H), 7.68-7.73 (m, 3H) 7.59 (d, J=8.0, 1H), 7.44-7.47 (m, 1H), 7.17-7.34 (m, 6H), 5.41 (s, 1H), 3.86 (s, 2H), 2.10 (br, 1H), 1.86 (br, 1H), 0.95 (br, 3H). $^{13}$C NMR (125 MHz, DMSO-$d_6$) δ 169.9, 166.1, 146.7, 141.8, 140.9, 139.2, 135.2, 131.4, 127.8, 126.7, 126.6, 125.5, 122.9, 122.0, 117.9, 113.2, 47.3, 33.4, 26.2, 11.9. HRMS calcd for $C_{26}H_{21}N_5OS$ 451.146; found 451.1474.

2-((5H-[1,2,4]triazino[5,6-b]indol-3-yl)thio)-1-(10H-phenoxazin-10-yl)butan-1-one (9): Compound 9 was synthesized similarly to 1. $^1$H NMR (500 MHz, DMSO-$d_6$) δ 12.63 (br, 1H), 8.33 (d, J=8.0, 1H), 7.70-7.34 (m, 3H), 7.60 (d, J=8.0, 1H), 7.46 (d, J=7.5, 1H), 7.19-7.25 (m, 6H), 5.47 (t, J=7.0, 1H), 1.99-2.03 (m, 1H), 1.81-1.86 (m, 1H), 0.89 (t, J=7.5, 3H). HRMS calcd for $C_{27}H_{19}N_5O_2S$ 453.1259; found 453.1270.

2-((5H-[1,2,4]triazino[5,6-b]indol-3-yl)thio)-1-(2H-benzo[b][1,4]thiazin-4(3H)-yl)butan-1-one (10): Compound 10 was synthesized similarly to 1. $^1$H NMR (500 MHz, $CDCl_3$) δ 10.15 (s, 1H), 8.38 (d, J=7.5, 1H), 7.60-7.66 (m, 3H), 7.43 (t, J=7.5, 1H), 7.23 (br, 1H), 7.12-7.14 (m, 2H), 5.30 (br, 1H), 3.30 (br, 3H), 2.14 (d, J=7.0, 1H), 2.00 (br, 2H), 1.08 (br, 3H). HRMS calcd for $C_{21}H_{19}N_5OS_2$ 421.1031; found 421.1038.

2-((5H-[1,2,4]triazino[5,6-b]indol-3-yl)thio)-1-(3,4-dihydroquinolin-1(2H)-yl)butan-1-one (11): Compound 11 was synthesized similarly to 1. $^1$H NMR (500 MHz, DMSO-$d_6$) δ 12.60 (br, 1H), 7.69-7.72 (m, 1H), 7.58 (d, J=8.0, 1H), 7.45 (t, J=7.0, 1H), 7.35 (br, 1H), 7.12-7.16 (m, 2H), 7.06 (t, J=7.5, 1H), 5.28 (t, J=6.5, 1H), 3.97 (br, 1H), 3.55 (br, 1H), 2.64-2.76 (m, 2H), 2.04 (br, 2H), 1.86 (br, 2H), 0.89 (br, 3H). HRMS calcd for $C_{22}H_{21}N_5OS$ 403.1467; found 403.1479.

2-((5H-[1,2,4]triazino[5,6-b]indol-3-yl)thio)-1-thiomorpholinobutan-1-one (12): Compound 12 was synthesized similarly to 1. $^1$H NMR (500 MHz, $CDCl_3$) δ 10.88 (br, 1H), 8.37 (d, J=8.0, 1H), 7.63-7.64 (m, 2H), 7.40-7.43 (m, 1H), 5.35 (t, J=7.0, 1H), 4.12-4.19 (m, 2H), 4.03-4.05 (m, 1H), 3.86-3.89 (m, 1H), 2.92-2.95 (m, 1H), 2.72-2.77 (m, 1H), 2.60-2.64 (m, 2H), 2.19-2.26 (m, 1H), 2.04-2.10 (m, 1H), 1.13 (t, J=7.0,3H). HRMS calcd for $C_{17}H_{19}N_5OS_2$ 373.1031; found 373.1033.

2-((5H-[1,2,4]triazino[5,6-b]indol-3-yl)thio)-1-(2,3-dihydro-1H-pyrrolo[3,2-b]pyridine-1-yl)butan-1-one (13): Compound 13 was synthesized similarly to 1. $^1$H NMR (500 MHz, DMSO-$d_6$) δ 12.56 (s, 1H), 8.28 (d, J=8.0, 1H), 8.08 (d, J=4.5, 1H), 7.67-7.71 (m, 2H), 7.56 (d, J=8.5, 1H), 7.42 (t, J=7.5, 1H), 7.00-7.03 (m, 1H), 6.59 (br, 1H), 4.05 (t, J=8.5, 2H), 3.12 (q, J=7.5, 2H), 2.10-2.15 (m, 1H), 1.98-2.04 (m, 1H), 1.07 (t, J=7.5, 3H). HRMS calcd for $C_{20}H_{18}N_6OS$ 390.1263; found 390.1274.

2-((5H-[1,2,4]triazino[5,6-b]indol-3-yl)thio)-1-(10H-phenothiazin-10-yl)hexan-1-one (14): Compound 14 was synthesized similarly to 1. $^1$H NMR (500 MHz, DMSO-$d_6$) δ 12.62 (br, 1H), 8.35 (d, J=7.5, 1H), 7.96 (br, 1H), 7.58-7.74 (m, 4H), 7.37-7.48 (m, 5H), 7.26 (br, 1H), 5.32 (t, J=7.0, 1H), 1.86 (br, 1H), 1.83 (br, 1H), 1.09-1.24 (m, 4H), 0.73 (br, 3H). HRMS calcd for $C_{27}H_{23}N_5OS_2$ 497.1344; found 497.1348.

2-((7-fluoro-5H-[1,2,4]triazino[5,6-b]indol-3-yl)thio)-1-(10H-phenothiazin-10-yl)butan-1-one (15): Compound 15 was synthesized similarly to compound 1. $^1$H NMR (500 MHz, DMSO-$d_6$) δ 12.70 (br, 1H), 8.17 (d, J=7.0, 1H), 7.89 (br, 1H), 7.56-7.64 (m, 4H), 7.37-7.43 (m, 4H), 7.22-7.25 (m, 1H), 5.26 (t, J=7.0, 1H), 1.95 (br, 1H), 1.74 (br, 1H), 0.85 (d, J=7.0, 3H). HRMS calcd for $C_{25}H_{18}FN_5OS_2$ 487.0937; found 487.0962.

2-((7-chloro-5H-[1,2,4]triazino[5,6-b]indol-3-yl)thio)-1-(10H-phenothiazin-10-yl)butan-1-one (16): Compound 16 was synthesized similarly to 1. $^1$H NMR (500 MHz, DMSO-$d_6$) δ 12.79 (br, 1H), 8.38 (s, 1H), 7.88 (br, 1H), 7.73-7.79 (m, 1H), 7.49-7.63 (m, 3H), 7.37-7.43 (m, 4H), 7.23 (br, 1H), 5.26 (t, J=7.0, 1H), 1.86 (br, 1H), 1.74 (br, 1H), 0.86 (br, 3H). HRMS calcd for $C_{25}H_{18}ClN_5OS_2$ 503.0641; found 503.0641.

2-((7-bromo-5H-[1,2,4]triazino[5,6-b]indol-3-yl)thio)-1-(10H-phenothiazin-10-yl)butan-1-one (17): Compound 17 was synthesized similarly to 1. $^1$H NMR (500 MHz, DMSO-$d_6$) δ 12.84 (br, 1H), 8.50 (s, 1H), 7.85 (d, J=8.0, 2H), 7.58 (d, J=8.5, 3H), 7.38-7.41 (m, 4H), 7.23 (br, 1H), 5.26 (s, 1H), 1.86 (br, 1H), 1.73 (br, 1H), 0.85 (br, 3H). HRMS calcd for $C_{25}H_{18}BrN_5OS_2$ 547.0136; found 547.0136.

2-((7-methoxy-5H-[1,2,4]triazino[5,6-b]indol-3-yl)thio)-1-(10H-phenothiazin-10-yl)butan-1-one (18): Compound 18 was synthesized similarly to 1. $^1$H NMR (500 MHz, DMSO-$d_6$) δ; 12.47 (br, 1H), 7.89 (br, 1H), 7.85 (br, 1H), 7.52-7.64 (m, 4H), 7.37-7.43 (m, 3H), 7.32-7.34 (m, 1H), 7.22 (br, 1H), 5.25 (t, J=7.0, 1H), 1.86 (br, 1H), 1.74 (br, 1H), 0.85 (br, 3H). HRMS calcd for $C_{26}H_{21}N_5O_2S_2$ 499.1137; found 499.1136.

2-((7-methyl-5H-[1,2,4]triazino[5,6-b]indol-3-yl)thio)-1-(10H-phenothiazin-10-yl)butan-1-one (19): Compound 19 was synthesized similarly to 1. $^1$H NMR (500 MHz, DMSO-$d_6$) δ 12.50 (br, 1H); 8.13 (s, 1H), 7.87 (br, 1H), 7.49-7.61 (m, 5H), 7.37-7.42 (m, 3H), 7.22 (br, 1H), 5.25 (d, J=6.5, 1H), 2.52 (s, 3H), 1.90 (br, 1H), 1.74 (br, H), 0.86 (br, 3H). HRMS calcd for $C_{26}H_{21}N_5OS_2$ 483.1188; found 483.1196

General procedure for synthesis of compounds 20-27.

5-(5-oxo-5-(3-((1-oxo-1-(10H-phenothiazin-10-yl)butan-2-yl)thio)-5H-[1,2,4]triazino[5,6-b]indol-5-yl)pentyl)tetrahydro-1H-thieno[2,3-d]imidazole-2(5H)-one (20). Biotin (100 mg, 0.410 mmol) was placed in 10 ml reaction flask and cooled to 0° C. 2.7 ml SOCl$_2$ was added to the flask and allowed to room temperature. The mixture was stirred for 1 h and excess SOCl$_2$ was evaporated. The residue was co-evaporated with 5 ml anhydrous toluene for three times to give the biotin acid chloride. The crude acid chloride was dissolved in 5 ml anhydrous THF. INZ (65 mg, 0.138 mmol) was dissolved in 3 ml anhydrous THF and injected to the above solution through syringe. The mixture was cooled to 0° C. and 100 μl Et$_3$N (0.717 mmol) was dropped to the mixture. The solution was then allowed to room temperature. TLC was used to monitor the reaction. After 11 h, TLC indicated that the reaction was completed. The reaction mixture was diluted with 30 ml ethyl acetate and washed by saturated NaCl for two times. The organic phase was separated and dried by anhydrous Na$_2$SO$_4$. The organic phase was filtered, concentrated in vacuum and was purified by column (DCM/CH$_3$OH, 55:1). The product was obtained as viscous oil. $^1$HNMR (500 MHz, CDCl$_3$) δ 8.69 (d, J=8.5, 1H), 8.40 (d, J=7.5, 1H), 7.92 (br, 1H), 7.75-7.72 (m, 1H), 7.67 (d, J=7.0, 1H), 7.59-7.56 (m, 1H), 7.53 (d, J=3.0, 1H), 7.40 (br, 1H), 7.35-7.29 (m, 3H), 7.18 (br, 1H), 5.60 (d, J=39.5, 1H), 5.42-5.38 (m, 1H), 5.14 (s, 1H), 4.56-4.53 (m, 1H), 4.41-4.37 (m, 1H), 3.48-3.41 (m, 1H), 3.35-3.26 (m, 1H), 3.25-3.23 (m, 1H), 2.98-2.95 (m, 1H), 2.76 (d, J=12.5, 1H), 1.90-1.83 (m, 4H), 1.79-1.75 (m, 1H), 1.70 (br, 1H), 1.61-1.58 (m, 2H), 0.98-0.90 (m, 3H). $^{13}$C NMR (125 MHz, CDCl$_3$) δ 173.1, 170.0, 167.7, 163.7, 146.7, 142.4, 139.5, 138.5, 138.3, 132.2, 127.7, 127.5, 127.3, 127.0, 126.8, 125.9, 121.4, 119.6, 117.8, 62.0, 60.4, 55.4, 55.3, 40.6, 39.1, 28.5, 28.4, 26.0, 24.2, 11.7. HRMS calcd for $C_{35}H_{33}N_7O_3S_3$ 695.1807; found 695.1817.

2-((5-benzoyl-5H-[1,2,4]triazino[5,6-b]indol-3-yl)thio)-1-(10H-phenothiazin-10-yl)butan-1-one (21): Compound 21 was synthesized similarly to 20. $^1$H NMR (500 MHz, DMSO-$d_6$) δ 8.49 (d, J=7.5, 1H), 8.23 (d, J=8.5, 1H), 7.60-7.78 (m, 6H), 7.40-7.55 (m, 4H), 7.17-7.28 (m, 4H), 7.06 (br, 1H), 4.89 (t, J=6.5, 1H), 1.93 (t, J=6.5, 1H), 1.57-1.62 (m, 1H), 0.75 (t, J=7.0, 3H). HRMS calcd for $C_{32}H_{23}N_5O_2S_2$ 573.1293; found 573.1298.

2-((5-nicotinoyl-5H-[1,2,4]triazino[5,6-b]indol-3-yl)thio)-1-(10H-phenothiazin-10-yl)butan-1-one (22): Compound 22 was synthesized similarly to 20. $^1$H NMR (500 MHz, CDCl$_3$) δ 8.97 (s, 1H), 8.91 (d, J=4.0, 1H), 8.49 (d, J=8.0, 1H), 8.41 (d, J=8.5, 1H), 8.03-8.05 (m, 1H), 7.78-7.84 (m, 2H), 7.66 (t, J=7.5, 1H), 7.58 (d, J=7.0, 1H), 7.48-7.51 (m, 2H), 7.34 (br, 1H), 7.26-7.28 (m, 3H), 7.12 (br, 1H), 5.08 (t, J=6.0, 1H), 1.94-1.96 (m, 1H), 1.67-1.70 (m, 1H), 0.83 (t, J=6.5, 3H). $^{13}$C NMR (125 MHz, CDCl$_3$) δ 169.9, 167.7, 166.4, 153.8, 150.6, 146.7, 141.9, 139.3, 138.4, 138.2, 137.3, 132.0, 129.6, 128.2, 127.7, 127.3, 127.2, 127.1, 126.9, 126.7, 126.2, 123.1, 121.9, 119.9, 116.5, 64.4, 25.8, 11.6. HRMS calcd $C_{31}H_{22}N_6O_2S_2$ 574.1246; found 574.1257.

1-(3-((1-oxo-1-(10H-phenothiazin-10-yl)butan-2-yl)thio)-5H-[1,2,4]triazino[5,6-b]indol-3-yl)hexan-1-one (23): Compound 23 was synthesized similarly to 20. $^1$H NMR (500 MHz, CDCl$_3$) δ 8.70 (d, J=8.5, 1H), 8.42 (d, J=8.0, 1H), 7.89 (br, 1H), 7.68-7.76 (m, 2H), 7.51-7.60 (m, 2H), 7.40 (br, 1H), 7.27-7.35 (m, 3H), 7.18 (br, 1H), 5.37 (t, J=7.0, 1H), 3.26-3.41 (m, 2H), 2.13 (br, 1H), 1.81-1.90 (m, 3H), 1.28-1.46 (m, 4H), 0.98-1.00 (m, 6H). HRMS calcd for $C_{31}H_{29}N_5O_2S_2$ 567.1763; found 567.1763.

1-(3-((1-oxo-1-(10H-phenothiazin-10-yl)butan-2-yl)thio)-5H-[1,2,4]triazino[5,6-b]indol-5-yl)pent-4-en-1-one (24): Compound 24 was synthesized similarly to 20. $^1$H NMR (500 MHz, CDCl$_3$) δ 8.71 (d, J=8.5, 1H), 8.43 (d, J=7.5, 1H), 7.89 (br, 1H), 7.73-7.77 (m, 1H), 7.68 (d, J=6.5, 1H), 7.58-7.61 (m, 1H), 7.51-7.53 (m, 1H), 7.41 (br, 1H), 7.34 (t, J=7.0, 1H), 7.26-7.28 (m, 2H), 7.18 (br, 1H), 5.90-5.98 (m, 1H), 5.36 (t, J=7.0, 1H), 5.10-5.20 (m, 2H), 3.48-3.53 (m, 1H), 3.37-3.43 (m, 1H), 2.57-2.62 (m, 2H), 2.12 (br, 1H), 1.89 (br, 1H), 0.98 (br, 3H). $^{13}$C NMR (125 MHz, CDCl$_3$) δ 172.5, 169.9, 167.8, 146.7, 142.4, 139.5, 138.6, 138.3, 136.2, 132.2, 128.3, 127.7, 127.4, 127.3, 126.9, 126.8, 125.9, 121.5, 119.6, 117.8, 116.3, 100.0, 45.8, 38.8, 28.2, 26.1, 11.7. HRMS calcd for $C_{30}H_{25}N_5O_2S_2$ 551.1450; found 551.1461.

1-(3-((1-oxo-1-(10H-phenothiazin-10-yl)butan-2-yl)thio)-5H-[1,2,4]triazino[5,6-b]indol-5-yl)pent-4-yn-1-one (25): Compound 25 was synthesized similarly to 20. $^1$H NMR (500 MHz, CDCl$_3$) δ 8.73 (d, J=8.5, 1H), 8.43 (d, J=7.5, 1H), 7.86 (d, J=7.0, 1H), 7.74-7.77 (m, 1H), 7.69 (d, J=7.0, 1H), 7.59-7.62 (m, 1H), 7.54 (d, J=7.5, 1H), 7.34-7.40 (m, 2H), 7.24-7.30 (m, 2H), 7.18 (br, 1H), 5.32 (t, J=7.0, 1H), 3.58-3.62 (m, 1H), 3.45-3.52 (m, 1H), 2.72-2.74 (m, 2H), 2.15 (br, 1H), 1.90 (br, 1H), 1.28 (t, J=7.5, 1H), 0.98-1.01 (m, 3H). HRMS calcd for $C_{30}H_{23}N_5O_2S_2$ 549.1293; found 549.1294.

5-bromo-1-(3-((1-oxo-1-(10H-phenothiazin-10-yl)butan-2-yl)thio)-5H-[1,2,4]triazino[5,6-b]indol-5-yl)pentan-1-one (26): Compound 26 was synthesized similarly to 20. $^1$H NMR (500 MHz, CDCl$_3$) δ 8.71 (d, J=8.5, 1H), 8.43 (d, J=7.5, 1H), 7.92 (br, 1H), 7.76 (t, J=8.0, 1H), 7.68 (d, J=7.0, 1H), 7.60 (t, J=7.5, 1H), 7.52-7.54 (m, 1H), 7.41 (br, 1H), 7.30-7.36 (m, 3H), 7.19 (br, 1H), 5.39 (t, J=7.0, 1H), 3.31-3.51 (m, 5H), 2.11 (br, 1H), 1.93-1.98 (m, 2H), 1.85-1.91 (m, 4H), 0.98 (br, 3H). HRMS calcd for $C_{29}H_{24}BrN_5O_2S_2$ 617.0555; found 617.0543.

Ethyl 5-oxo-5-(3-((1-oxo-1-(10H-phenothiazin-10-yl)butan-2-yl)thio)-5H-[1,2,4]triazino[5,6-b]indol-5-yl)pentanoate (27): Compound 27 was synthesized similarly to 20. $^1$H NMR (500 MHz, CD$_3$Cl) δ 8.70 (d, J=8.5, 1H), 8.42 (d, J=7.5, 1H), 7.91 (br, 1H), 7.74-7.77 (m, 1H), 7.68 (d, J=7.5, 1H), 7.58-7.61 (m, 1H), 7.52-7.53 (m, 1H), 7.40 (br, 1H), 7.30-7.35 (m, 3H), 7.17 (br, 1H), 5.39 (t, J=6.5, 1H), 3.74 (s, 3H), 3.71-3.72 (m, 2H), 3.42-3.52 (m, 2H), 2.42-2.50 (m, 2H), 1.89-2.02 (m, 2H), 0.98 (br, 3H). $^{13}$C NMR (125 MHz, CD$_3$Cl) δ 173.3, 172.5, 169.9, 167.7, 146.6, 142.4, 139.4, 138.6, 138.3, 132.2, 128.3, 127.7, 127.5, 127.3, 127.1, 170.0, 126.8, 125.9, 121.4, 119.6, 117.7, 68.0, 51.8, 38.4, 32.9, 26.0, 19.5, 11.7. HRMS calcd for C$_{31}$H$_{27}$N$_5$O$_4$S$_2$ 597.1504; found 597.1498.

General Procedure for Synthesis of Compounds 28-36

Ethyl 2-(3-((1-oxo-1-(10H-phenothiazin-10-yl)butan-2-yl)thio)-5H-[1,2,4]triazino[5,6-b]indol-5-yl)acetate (28): Compound 5 (0.1407 g, 0.3 mmol) was dissolved in 5 ml anhydrous DMF. 50 mg K$_2$CO$_3$ and ethyl 2-bromoacetate (0.2004 g, 1.2 mmol) were added to the above solution. This reaction was stirred at room temperature. After 6 h, TLC indicated there was no starting material remained and the reaction was stopped. 150 ml ethyl acetate was added to the above mixture. The organic phase was washed by saturated NH$_4$Cl for five times. The organic phase was dried by Na$_2$SO$_4$ and concentrated. The residue was purified by flash column chromatography (hexane/ethyl acetate-2:1) and viscous oil 28 was obtained. $^1$H NMR (500 MHz, CDCl$_3$) δ 8.39 (d, J=7.5, 1H), 7.88 (br, 1H), 7.62-7.63 (m, 2H), 7.42-7.45 (m, 2H), 7.29-7.32 (m, 2H), 7.19-7.26 (m, 2H), 7.09 (br, 2H), 5.37 (t, J=7.0, 1H), 4.97 (s, 2H), 4.19 (q, J=7.0, 2H), 2.01 (br, 1H), 1.82 (br, 1H), 1.20-1.23 (m, 3H), 0.89-0.91 (m, 3H). HRMS calcd for C$_{29}$H$_{25}$N$_5$O$_3$S$_2$ 555.1399; found 555.1405.

2-(3-((1-oxo-1-(10H-phenothiazin-10-yl)butan-2-yl)thio)-5H-[1,2,4]triazino[5,6-b]indol-5-yl)acetic acid (29): Compound 28 (161 mg, 0.2901 mmol) was dissolved in 15 ml 1,4-dioxane and 0.58 ml 1 M NaOH was added to the solution. The reaction mixture was stirred at room temperature. After 14 h, TLC indicated that there was no starting material remained and the reaction was stopped. The pH of the reaction was adjusted to 4-5 using concentrated HAc. The mixture was extracted by ethyl acetate for three times and the organic phase was combined. The organic phase was dried by anhydrous Na$_2$SO$_4$ and concentrated under vacuum. The residue was purified by column (DCM/MeOH-60:1) and the viscous oil 29 was obtained. $^1$H NMR (500 MHz, CDCl$_3$) δ 8.42 (d, J=8.0, 1H), 7.94 (br, 1H), 7.62-7.68 (m, 2H), 7.35-7.49 (m, 4H), 7.24-7.30 (m, 3H), 7.07 (br, 1H), 5.40 (t, J=7.0, 1H), 5.01 (s, 2H), 2.03 (br, 1H), 1.84 (br, 1H), 0.92 (br, 3H). HRMS calcd for C$_{27}$H$_{21}$N$_5$O$_3$S$_2$ 527.1086. found 527.1093.

2-((5(2-hydroxyethyl)-5H-[1,2,4]triazino[5,6-b]indol-5-yl)thiol)-1-(10H-phenothiazin-10-yl)butan-1-one (30): Compound 28 (95 mg, 0.1712 mmol) was dissolved in 4 ml MeOH/THF (3:1). The solution was cooled to 0° C. Then NaBH$_4$ (39 mg, 1.027 mmol) was added to the above solution. The reaction mixture was allowed to room temperature. After 6 h, TLC indicated there was no starting material remained and the reaction was stopped. Acetic acid was used to quench the reaction. The mixture was purified by column (hexane/ethyl acetate (5:1-3:1-1:1) and the viscous oil was obtained. $^1$H NMR (500 MHz, CDCl$_3$) δ 8.44 (d, J=8.0, 1H), 7.99 (br, 1H), 7.72 (t, J=8.0, 1H), 7.66 (br, 1H), 7.59 (d, J=8.0, 1H), 7.47-7.51 (m, 2H), 7.40 (br, 1H), 7.27-7.34 (m, 3H), 7.18 (br, 1H), 5.37 (br, 1H), 4.45 (br, 2H), 4.09 (br, 2H), 2.28 (br, 1H), 2.12 (br, 1H), 1.88 (br, 1H), 0.96 (d, J=7.5, 3H). $^{13}$C NMR (125 MHz, CDCl$_3$) δ 170.4, 146.7, 141.6, 138.6, 138.4, 130.9, 127.7, 127.3, 127.2, 126.9, 126.8, 123.1, 122.4, 110.6, 100.0, 60.7, 44.2, 25.9, 11.7. HRMS calcd for C$_{27}$H$_{23}$N$_5$O$_2$S$_2$ 513.1293. found 513.1303.

1-(10H-phenothiazin-10-yl)-2-((5(prop-2-yn-1-yl)-5H-[1,2,4]triazino[5,6-b]indol-3-yl)thiol)butan-1-one (31): Compound 31 was synthesized similarly to 28 as amorphous powder. $^1$H NMR (500 MHz, CDCl$_3$) δ 8.48 (d, J=7.5 1H), 7.59 (br, 1H), 7.75-7.78 (m, 1H), 7.67-7.70 (m, 2H), 7.51-7.55 (m, 2H), 7.40 (br, 1H), 7.31-7.34 (m, 3H), 7.17 (br, 1H), 5.43 (t, J=6.5, 1H), 5.08-5.13 (m, 2H), 2.40 (s, 1H), 1.92 (br, 1H), 1.89 (br, 1H), 0.92-1.01 (m, 3H). HRMS calcd for C$_{28}$H$_{21}$N$_5$O$_2$S$_2$ 507.1188; found 507.1188.

2-((5(but-3-yn-1-yl)-5H-[1,2,4]triazino[5,6-b]indol-3-yl)thiol)-1-(10H-phenothiazin-10-yl)butan-1-one (32): Compound 32 was synthesized similarly to 28 as amorphous powder. $^1$H NMR (500 MHz, CDCl$_3$) δ 8.46 (d, J=7.5, 1H), 7.97 (br, 1H), 7.68-7.74 (m, 2H), 7.48-7.59 (m, 3H), 7.40 (br, 1H), 7.31-7.34 (m, 2H), 7.18 (br, 1H), 5.41 (t, J=7.0, 1H), 4.45-4.52 (m, 2H), 2.77-2.80 (m, 2H), 2.14 (br, 1H), 1.89 (br, 1H), 0.98 (br, 3H). $^{13}$C NMR (125 MHz, CD$_3$Cl) δ 169.4, 165.9, 145.8, 140.9, 140.6, 137.9, 137.8, 130.9, 128.2, 127.8, 127.5, 127.2, 127.0, 123.0, 121.5, 117.3, 111.6, 80.6, 73.3, 25.7, 17.5, 11.3. HRMS calcd for C$_{28}$H$_{21}$N$_5$O$_2$S$_2$ 507.1188; found 507.1188.

2-((5-(2-oxo-2-phenylethyl)-5H-[1,2,4]triazino[5,6-b]indol-3-yl)thiol)-1-(10H-phenothiazin-10-yl)butan-1-one (33): Compound 33 was synthesized similarly to 28 as amorphous powder. $^1$H NMR (500 MHz, CDCl$_3$) δ 8.49 (d, J=7.5, 1H), 8.05 (d, J=7.5, 1H), 7.90 (br, 1H), 7.65-7.72 (m, 3H), 7.55-7.58 (m, 2H), 7.49-7.52 (m, 2H), 7.40-7.46 (m, 2H), 7.31-7.39 (m, 1H), 7.21-7.24 (m, 4H), 5.69-5.77 (m, 2H), 5.39 (t, J=6.5, 1H), 2.05 (br, 1H), 1.87 (d, J=5.5, 1H), 0.90-0.92 (m, 3H). HRMS calcd for C$_{33}$H$_{25}$N$_5$O$_2$S$_2$ 587.1450; found 507.1461.

2-((5-((1-phenethyl-1H-1,2,3-triazol-4-yl)methyl)-5H-[1,2,4]triazino[5,6-b]indol-3-yl)thiol)-1-(10H-henothiazin-10-yl)butan-1-one (34): 2-bromoethylbenzene (3.083 g, 0.3 mmol) was dissolved in 17 ml anhydrous DMF. NaN$_3$ (2.1664 g, 33.329 mmol) and 56 mg KI were added to the above solution. The reaction mixture was heated to 90° C. for 18 h. TLC indicated that there was no starting material remained. The reaction was stopped and 200 ml DCM was added to the mixture. The organic phase was washed by 50 ml water and dried by anhydrous Na$_2$SO$_4$. The organic phase was concentrated and evaporated under vacuum. The crude azide was obtained and used for the next step directly.

Compound 32 (0.1268 g, 0.25 mmol) and azide (33.4 mg, 0.227 mmol) were dissolved in 3.6 ml t-BuOH/H$_2$O/THF (v/v-1:1:1). Sodium ascorbate (98.9 mg, 0.4994 mmol) and CuSO$_4$ (11.3 mg, 0.0454 mmol) in 0.5 ml water were added to the above reaction mixture. The reaction mixture was heated to 55° C. After stirring for 24 h, TLC indicated that there was no starting material remained. The reaction was stopped and cooled to room temperature. 6 ml water was added to the mixture. The solid was collected and washed with a few water. Then, the solid was dissolved in 8 ml acetone and the solution was filtered. The filtrate was evaporated and the residue was dissolved in 3 ml ethyl acetate. The solution was heated and 5 ml hexane was added to the solution. After overnight, gray solid was formed and collected. The amorphous solid 34 was washed by 4 ml hexane and dried. $^1$H NMR (500 MHz, CDCl$_3$) δ 8.44 (d, J=8.0, 1H), 8.03 (br, 1H), 7.66-7.77 (m, 3H), 7.48-7.51 (m, 2H), 7.41 (br, 1H), 7.32-7.33 (m, 2H), 7.18 (br, 1H), 7.06-7.13 (m, 4H), 6.93-6.95 (m, 2H), 5.46-5.56 (m, 3H), 4.53 (t, J=7.5, 2H), 3.14 (t, J=7 0.5?, 2H), 2.07 (br, 1H), 1.88 (br, 1H), 0.98 (br, 3H). HRMS calcd for C$_{36}$H$_{30}$N$_8$OS$_2$ 654.1984; found 654.1991.

2-((5-((1-phenethyl-1H-1,2,3-triazol-4-yl)ethyl)-5H-[1,2,4]triazino[5,6-b]indol-3-yl)thiol)-1-(10H-phenothiazin-10-yl)butan-1-one (35): Compound 35 was synthesized similarly to 34 as amorphous powder. $^1$H NMR (500 MHz, CDCl$_3$) δ 8.43 (d, J=7.5, 1H), 8.00 (br, 1H), 7.64-7.67 (m, 2H), 7.42-7.50 (m, 4H), 7.23-7.33 (m, 6H), 7.18 (br, 1H), 7.00-7.02 (m, 2H), 6.92 (s, 1H), 5.44 (t, J=6.5, 1H), 4.62 (t, J=7.0, 2H), 4.48 (t, J=7.5, 2H), 3.24 (t, J=7.0, 2H), 3.06 (t, J=7.5, 2H), 2.04-2.08 (m, 1H), 1.87-1.89 (m, 1H), 0.92-1.01 (m, 3H). HRMS calcd for C$_{37}$H$_{32}$N$_8$OS$_2$ 668.2140; found 668.2135.

Ethyl 4-(4-(2-(3-((1-oxo-1-(10H-phenothiazin-10-yl)butan-2-yl)thio)-5H-[1,2,4]triazino[5,6-b]indol-5-yl)ethyl)-1H-1,2,3-triazol-1-yl)butanoate (36): Compound 36 was synthesized similarly to 34 as amorphous powder. $^1$H NMR (500 MHz, CDCl$_3$) δ 8.41 (d, J=8.0, 1H), 8.01 (br, 1H), 7.62-7.68 (m, 2H), 7.50 (d, J=7.5, 1H), 7.40-7.44 (m, 3H), 7.26-7.33 (m, 3H), 7.17 (br, 2H), 5.44 (t, J=6.5, 1H), 4.66 (t, J=7.0, 2H), 4.32 (t, J=7.0, 2H), 4.15 (q, J=7.0, 2H), 3.29 (t, J=7.0, 2H), 2.20 (t, J=7.5, 2H), 2.07-2.11 (m, 2H), 1.87 (br, 1H), 1.77 (br, 1H), 1.28 (t, J=7.0, 3H), 0.94-1.00 (m, 3H). HRMS calcd for C$_{35}$H$_{34}$N$_8$O$_3$S$_2$ 678.2195; found 678.2197.

1-(acridin-10(9H)-yl)-2-((5-(2-hydroxyethyl)-5H-[1,2,4]triazino[5,6-b]indol-3-yl)thio)butan-1-one (37): Compound 37 was synthesized similarly to 30 as viscous oil. 1H NMR (500 MHz, CDCl$_3$) δ 8.35 (d, J=7.5, 1H), 7.77 (br, 2H), 7.66-7.70 (m, 1H), 7.55 (d, J=8.0, 1H), 7.44 (t, J=8.0, 1H), 7.24-7.29 (m, 4H), 7.16 (br, 2H), 5.47 (br, 1H), 4.33-4.41 (m, 2H), 4.05-4.08 (m, 2H), 3.86 (br, 2H), 2.13-2.19 (m, 1H), 1.98-1.99 (m, 1H), 1.04 (br, 3H). HRMS calcd for C$_{28}$H$_{25}$N$_5$O$_2$S 495.1729; found 495.1731.

Figure 14:
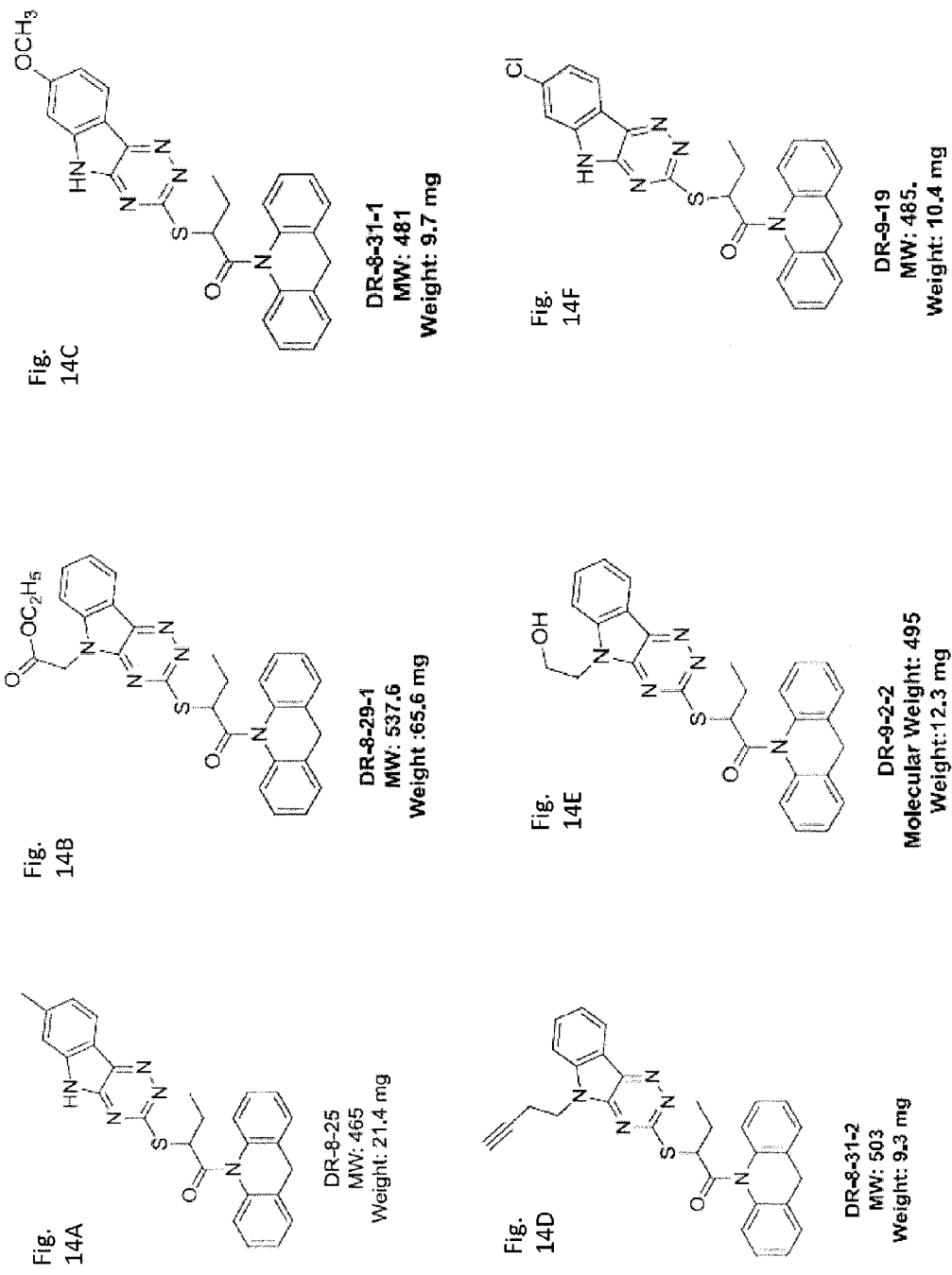

The structures of additional INZ analogs are provided in FIGS. 14A-14 F. FIG. 14A illustrates the structure of INZ synthetic analog 38, having a molecular weight of 465. FIG. 14B illustrates the structure of INZ synthetic analog 39, having a molecular weight of 537.6. FIG. 14C illustrates the structure of INZ synthetic analog 40, having a molecular weight of 481. FIG. 14D illustrates the structure of INZ synthetic analog 41, having a molecular weight of 503. FIG. 14E illustrates the structure of INZ synthetic analog 42, having a molecular weight of 495. FIG. 15A shows mass spectrometry characterization data for INZ synthetic analog 42. FIG. 15A shows liquid chromatography characterization data for INZ synthetic analog 42. FIG. 14F illustrates the structure of INZ synthetic analog 43, which has a molecular weight of 485.

The Effect of Compound 8 (Also Called INZ-14) on the Growth of H460 Orthotopic Lung Tumors.

By SAR analysis and chemical optimization, the solubility of INZ was improved and it was also found that INZ-14 (compound 8) was over 2 fold more active than INZ in growth inhibition of HCT116+/+ cells (EC$_{50}$=1.41 μM and 3.52 μM, respectively). The EC$_{90}$ values of this analog were in the range of 10 μM, which were 5 fold lower than INZ (FIG. 12). Compound 37 was found to be more potent than INZ without observed toxicity in cell based and in vivo biochemical toxicity assays. As shown in FIG. 12A, cell growth inhibition curves of INZ and compound 37 in H460 cells. EC$_{50}$ and EC$_{90}$ values represent the average of triplicates within 10% relative standard deviation. The results were repeated in two independent experiments. As shown in FIG. 12B, compound 37 was administered i.p. at 50 mg/kg once per day for two weeks in C57BL/6 and their blood was collected for Alanine transferase and total bilirubin biochemical assay.

In a preclinical trial experiment using the established orthotopic lung cancer model, INZ-14 (compound 8) was not only more potent than INZ in p53 activation and inhibition of cell proliferation than INZ, but also exhibited highly promising bioactivity against orthotopic lung cancers (FIG. 13). The effects of compound 8 on the growth of H460 orthotopic lung tumors. Each mouse was dosed once a day via i.p. with either vehicle or 14 (50 mg/kg) for 3 weeks starting 4 days after implantation of 5×10$^5$ H460-Luc tumor cells into the pleural space of the SCID mice. As shown in FIG. 13A, tumor burden in lung area measured by bioluminescent imaging (BLI) for each treatment group. Each value is a mean of five animals ±SD. As shown in FIG. 13B, bioluminescent imaging (BLI) of orthotopic lung tumors in SCID mice.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A composition, comprising: a compound according to Formula (I) or a pharmaceutically acceptable salt thereof;

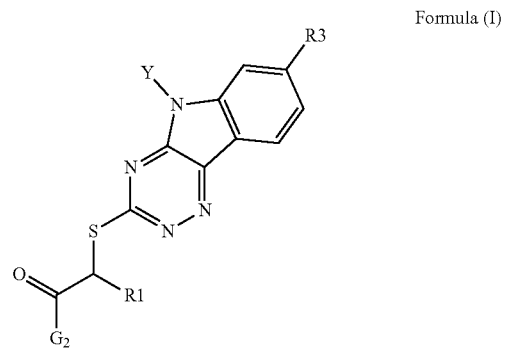

Formula (I)

wherein, G$_2$ is and X is CH$_2$ or S;
wherein when X is CH$_2$;
R1 is CH$_3$CH$_2$;
Y is: H, CH$_2$OH, or CH$_2$CH$_2$OH;
R3 is H;
R4 is H; and wherein when X is S;
R1 is CH₃CH₂;
Y is:

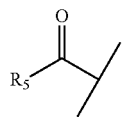

or R2;
R2 is:

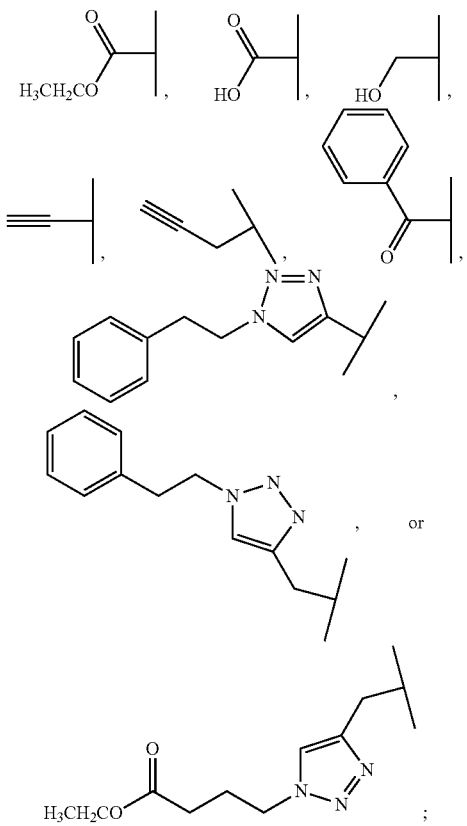

R3 is H;
R4 is H; and
R5 is:

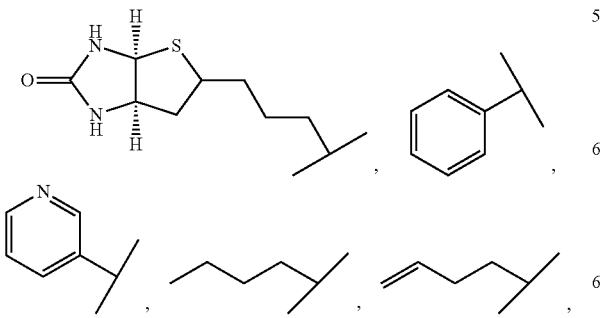

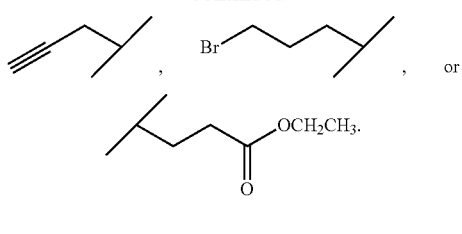

2. The composition according to claim 1, wherein the compound according to Formula I is:

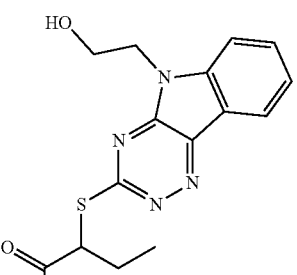

or a pharmaceutically acceptable salt thereof.

3. The composition according to claim 1, wherein G₂ is

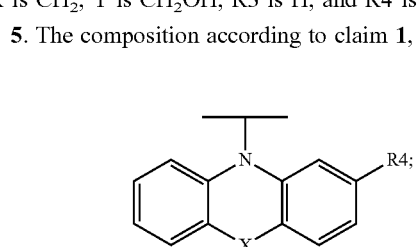

X is CH₂, R1 is CH₃CH₂, Y is H, R3 is H, and R4 is H.

4. The composition according to claim 1, wherein G₂ is

X is CH₂, Y is CH₂OH, R3 is H, and R4 is H.

5. The composition according to claim 1, wherein G₂ is:

X is: S;
R1 is: CH₃CH₂;
Y is:

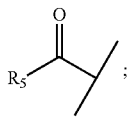

R3 is H;
R4 is H; and
R5 is:

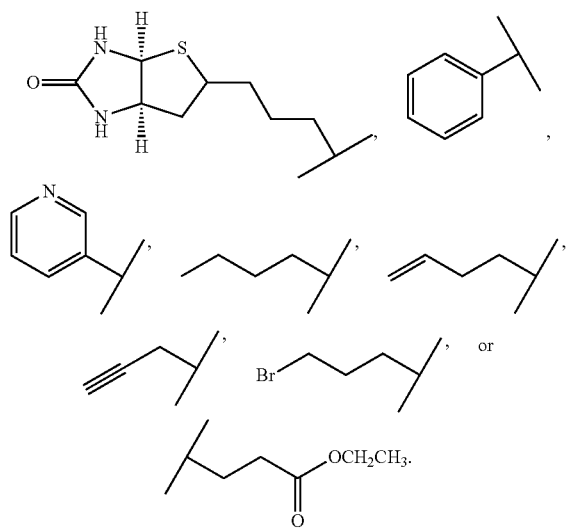

6. The composition according to claim 1, wherein G₂ is:

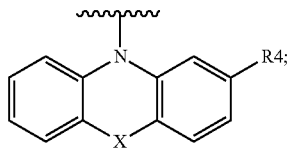

X is: S;
R1 is: CH₃CH₂;
Y is: R2;
R2 is:

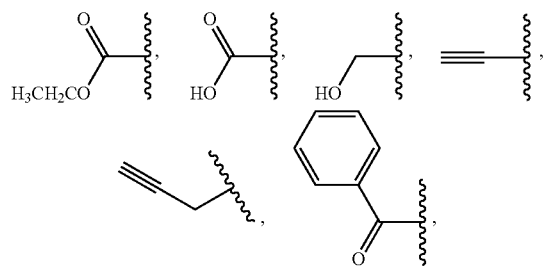

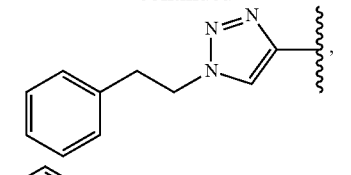

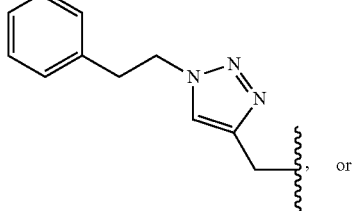

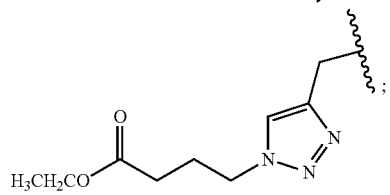

R3 is H; and
R4 is H.

7. A method of increasing apoptosis, comprising the steps of;
contacting at least one eukaryotic cell with an effective amount of a compound according to Formula (I) or a pharmaceutically acceptable salt thereof;

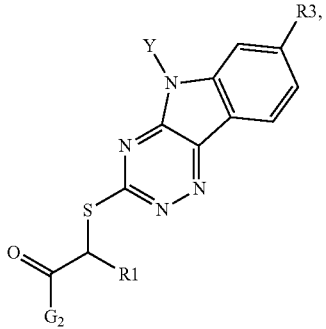

Formula (I)

wherein the compound of Formula I is:

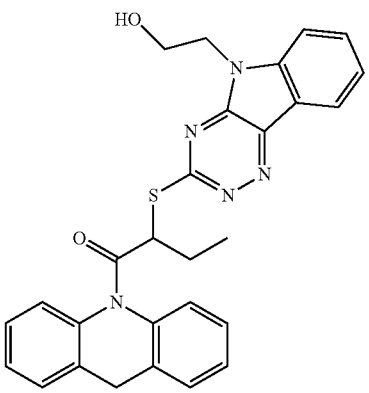 [SMILES: CCC(Sc1nnc2c3ccccc3n(CCO)c2n1)C(=O)N1c2ccccc2Cc2ccccc21]

or a pharmaceutically acceptable salt thereof.

8. A method of treating a human or an animal, comprising the steps of:

administering at least one therapeutically effective dose of a compound according to Formula (I) or a pharmaceutically acceptable salt thereof;

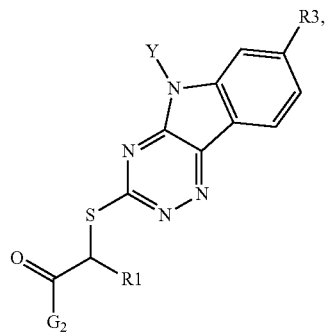

Formula (I)

wherein the compound according to Formula I is:

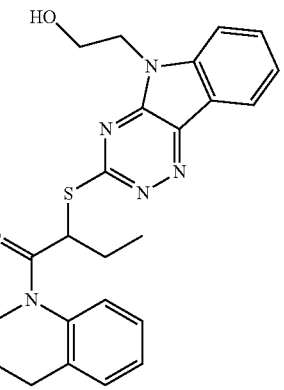

or a pharmaceutically acceptable salt thereof;
wherein the human or animal has been diagnosed with cancer, and wherein the cancer is lung cancer.

* * * * *